US006934836B2

(12) United States Patent
Strand et al.

(10) Patent No.: US 6,934,836 B2
(45) Date of Patent: Aug. 23, 2005

(54) FLUID SEPARATION CONDUIT CARTRIDGE WITH ENCRYPTION CAPABILITY

(75) Inventors: David Strand, Sherborn, MA (US); Peter Myers, Bromborough (GB); Tim Myers, Bromborough (GB)

(73) Assignee: Protasis Corporation, Marlborough, MA (US)

( * ) Notice: Subject to any disclaimer, the term of this patent is extended or adjusted under 35 U.S.C. 154(b) by 689 days.

(21) Appl. No.: 10/034,757

(22) Filed: Dec. 27, 2001

(65) Prior Publication Data

US 2002/0199094 A1 Dec. 26, 2002

Related U.S. Application Data

(63) Continuation of application No. PCT/US01/31295, filed on Oct. 5, 2001.
(60) Provisional application No. 60/239,010, filed on Oct. 6, 2000, provisional application No. 60/239,063, filed on Oct. 6, 2000, provisional application No. 60/238,805, filed on Oct. 6, 2000, and provisional application No. 60/238,390, filed on Oct. 6, 2000.

(51) Int. Cl.$^7$ .............................................. G06F 17/00
(52) U.S. Cl. ...................... 713/150; 713/193; 713/194
(58) Field of Search ................................ 713/189–194, 713/150–153, 182–186

(56) References Cited

U.S. PATENT DOCUMENTS

| 4,975,647 A | 12/1990 | Downer et al. |
| 5,519,635 A | 5/1996 | Miyake et al. |
| 5,889,197 A | 3/1999 | Van der Maas et al. |
| 5,892,458 A | 4/1999 | Anderer et al. |

OTHER PUBLICATIONS

Reactions of high lead solders with BIOACT EC–7R semi–aqueous cleaning reagents Wong, C.P.; Gillum, W.O.; Walters, R.A.; Sakach, P.J.; Powell, D.; Bivins, B.; Components, Packaging, and Manufacturing Technology, Part C, IEEE Transactions on see also Compo.*
Diffusion of low molecular weight fluid in EPDM Liwen Cao; Hackam, R.; Electrical Insulation and Dielectric Phenomena, 1998. Annual Report. Conference on , vol. 1, Oct. 25–28 1998.*
An integrated LC–ESI chip with electrochemical–based gradient generation Jun Xie; Jason Shih; Changlin Pang; Yu–Chong Tai; Yunan Miao; Lee, T.D.; Micro Electro Mechanical Systems, 2004. 17th IEEE International Conference on. (MEMS), 2004.*
Notification of Transmittal of the International Search Report or the Declaration (7pgs).
Modular, Digital, Gas Analyzer Architecture Re–Thinking the Approach to Analytical Measurements vol. 49, Part 2, 1994, (pp. 197–208).

* cited by examiner

Primary Examiner—David Jung
(74) Attorney, Agent, or Firm—Banner & Witcoff, Ltd.

(57) ABSTRACT

A fluid separation conduit cartridge that is operative to encrypt, decrypt, transmit and receive information is disclosed. The conduit cartridge encrypts information sent to an analytical system or an operating facility in communication with the conduit cartridge and can decrypt encrypted information received from an analytical system or an operating facility in communication with the conduit cartridge.

31 Claims, 23 Drawing Sheets

FLUID SEPARATION CONDUIT CARTRIDGE WITH ENCRYPTION CAPABILITY

This is a continuation of International Application No. PCT/US10/31295 filed on Oct. 05, 2001 and titled "Fluid Separation Conduit Cartridge with Encryption Capability."

CROSS-REFERENCED APPLICATIONS

This application claims priority to commonly assigned U.S. Patent Application No. 60/239,010 titled "Microfluidic Substrate Assembly and a Method for Making Same" and filed on Oct. 06, 2000, commonly assigned U.S. Patent Application No. 60/239,063 titled "Liquid Separation Column Smart Cartridge" and filed on Oct. 06, 2000, commonly assigned U.S. Patent Application No. 60/238,805 titled "Liquid Separation Column Smart Cartridge with Encryption Capability" and filed on Oct. 06, 2000, and commonly assigned U.S. Patent Application No. 60/238,390 titled "Microfluidic Substrate Assembly and a Method for Making Same" and filed on Oct. 06, 2000, the entire disclosure of each of which is hereby incorporated herein by reference for all purposes.

FIELD OF INVENTION

This invention pertains to a fluid separation conduit cartridge, in particular, to a fluid chromatography conduit cartridge that has the ability to encrypt, compress, transmit, receive, and decrypt information.

BACKGROUND

Molecules can be separated effectively by employing liquid chromatography ("LC"). A typical liquid chromatography system consists of a column and solvent that traverses the entire column. High pressures are usually required to pump solvent through the column leading to the development of high pressure or high performance liquid chromatography (HPLC). High performance liquid chromatography systems typically consist of high pressure pumps, at least one solvent reservoir, a column capable of withstanding relatively high pressures, and a detector. Columns used in HPLC typically consist of packing material. In most instances this packing material includes silica-based particles typically with functional groups (defining a column's chemistry) attached to these silica-based particles. The packing of the column is a critical event in the construction of a specific column, for the integrity of the packed bed impacts the overall resolution capability of the column. As the bed becomes disrupted through any series of events, for example, sharp periodic fluctuations in column pressure, resolution will decrease. Maintaining the integrity of the packing bed is essential if the original efficiency capability of a particular column is to be preserved. Through continued usage, the column's packed bed and the bonded phase deteriorate, and the= resolving power of the column is then lost. Detection and recordation of this loss of resolving power is very important.

Capillary liquid chromatography is a micro-version of traditional liquid chromatography. As is true for traditional liquid chromatography, the column used in capillary liquid chromatography is of critical import. These columns typically have low solvent consumption and require low volumes of sample for analysis. These conditions translate into a higher degree of unit mass detectability. Capillary liquid chromatography systems typically comprise a micro-pumping unit, a capillary column, a detector, and a data processing system. Capillary liquid chromatography columns are typically produced using such materials as fused silica, stainless steel, or polymeric compositions. The lumen of the capillary is packed with packing material containing separation material, such as bonded silica particles. Typically, the internal diameter of the capillary column is between 50 and 500 $\mu$m.

Assessment of column quality is performed typically by running standard analytes through the column and comparing certain chromatographic parameters to a standard test run. Apart from performing a chromatographic run with known analytes, assessment of the column cannot be effectuated. Currently, columns themselves lack the ability to store their performance information which can be of great value. The performance record of a column is very important in environments where quality control is an issue, for example, in the pharmaceutical industry. The increased automation and remote placement of analytical devices requires that the information obtained by or sent to the analytical devices remains secure. Since the information may contain corporate trade secrets and/or other sensitive information, precautionary methods must be implemented to prevent the inadvertent dissemination of any information obtained by, transmitted to, or sent by a remote analytical device. Efficient automated field sampling and analyses are not possible without the ability to send the acquired information securely, rapidly, and remotely.

There exists a great need in the art, for a fluid separation conduit cartridge that can compress, encrypt, transmit, and receive information. Such a device would provide for automated remote analyses. There also exists a great need for a conduit cartridge that can accept encrypted messages, so that the method or parameters of the cartridge, or methods used by an instrument in communication with the conduit cartridge may be altered without having to retrieve the remotely placed conduit cartridge.

SUMMARY

In accordance with a first aspect, a fluid separation conduit cartridge (also referred to below as a conduit cartridge) comprises at least a housing unit, a memory unit, and one or more connectors is disclosed. In preferred embodiments, the housing unit is manufactured from materials capable of withstanding high pressures and harsh environments. For example, the housing unit can be manufactured from steel, e.g. stainless steel or galvanized steel, such that rusting is minimized and strength is increased. In other embodiments, the housing unit is manufactured from plastics or polymers, such as polyetheretherketone (PEEK) for example, such that the housing unit and components within the housing unit can be assembled rapidly, to minimize assembly costs, and to provide a lightweight device. The housing unit typically has one or more connectors, as described in detail below, to connect the conduit cartridge with a system, instrument or other device. The connectors are operative to create a fluid-tight seal between the conduit cartridge and any device to which the conduit cartridge is interfaced, e.g. attached. As used here fluid refers to liquids and/or gases, e.g. supercritical fluids, etc., optionally containing particulate matter, dissolved species, solvated species, and the like. As used here, memory unit refers to any device that is operative to store, read, write, and/or read and write information. As used here information refers to any data, results, parameters, etc. used or generated by an instrument or fluid separation conduit cartridge, e.g. manufacturing information, usage information, test results, and the like. Preferred memory units include but are not limited to memory chips, e.g., read only memory (ROMs), programmable read-only memory (ROMs) erasable programmable read-only memory (EPROMs), electrically erasable programmable read-only memory (EEPROMs), DIMMs, SIMMs, and other memory units and memory chips well known to those skilled in the art and commercially available from numerous manufacturers such as Siemens, Toshiba, Texas Instruments and Micron. In certain embodiments, the memory unit is integrally attached to the conduit cartridge, for example, at the time of its manufacture. In other embodiments, the memory unit may be removed and upgraded, for example, to a larger memory unit. In yet other embodiments, the memory unit is a component of a larger device or circuit, e.g. a circuit comprising a microprocessor in electrical communication with the memory unit, for example. One skilled in the art given the benefit of this disclosure will be able to select suitable memory units for incorporation into the conduit cartridges disclosed here. The amount of information stored typically will depend upon the memory capacity, and how the information is recovered will depend on whether or not a microcontroller, e.g. a microprocessor, is incorporated in the memory unit itself or is in electrical communication with the memory unit. Components could be read-only or read/write or be partitioned with a read-only area for manufacturing information and a read/write area for usage information. The information stored could vary from the minimal amount of data required to identify the cartridge and its quality control test performance, e.g. in text format, to a full quality control trace and usage history.

In accordance with another aspect, the fluid separation conduit cartridge may comprise a plurality of memory units. For example, a first memory unit may be specific for use on a specific analytical system, e.g. a specific chromatography system. This type of memory unit is customized for use with a specific manufacturer's analytical system. That is, the memory unit may be chosen such that it is compatible with or contains information such that the conduit cartridge is operative with a specific analytical system, e.g. a Waters Alliance HPLC System or a Varian SD-2 Prep HPLC System, for example. The first memory unit may be readable and writeable. Preferably, the read-only area includes at least full conduit cartridge manufacturing and quality control test data. The writeable area can include at least a history of cartridge usage, number of injections, maximum used pressure, maximum used flow rate, pressure/flow profile, maximum temperature, serial number, cartridge parameters, e.g. number of theoretical plates, test results, or the like, as well as other features. A second memory unit is chosen such that the memory unit is operative with any analytical system. For example, the memory unit is a read-only memory unit and is supplied with a device to read the information in the memory unit and output the information in via, for example, a RS232 interface. The information may include but is not limited to cartridge manufacturing and quality control test data, conduit cartridge history, and the like.

In accordance with another aspect, the fluid separation conduit cartridge comprises a housing unit, a fluid separation conduit defined within the housing unit and a ferrule subassembly, as described above, at the housing inlet orifice and/or outlet orifice. The fluid separation conduit may be defined or formed, for example, by a lumen or tube, e.g., a flexible tube. Typically such tube is connected at one end to the inlet orifice and at the other end at the outlet orifice. The fluid separation conduit, or a portion thereof, may be defined by a channel formed from assembling individual layers into a multi-layer laminated substrate, such as the fluid handling substrates described in commonly assigned U.S. Patent Application No. 60/239,010 titled "Microfluidic Substrate Assembly and a Method of Making Same" and filed on Oct. 06, 2000, the entire disclosure of which is hereby incorporated by reference for all purposes. In certain embodiments, the fluid separation conduit comprises one or more flexible tubes that terminate at opposite ends of a channel formed by assembling the layers of a multi-layer laminated substrate. That is, in certain embodiments the fluid separation conduit comprises at least one flexible tube in fluid communication with at least one channel, where the fluid separation conduit is defined by the at least one tube and the channel. The fluid separation conduit has at least first and second openings for entry and exit of fluid, respectively. The cross-sectional diameter of the fluid separation conduit may vary depending on the desired flow rate, desired operation pressure, conduit shape, and the like. For example, for a cylindrical fluid separation conduit comprising a flexible tube, e g. a coiled capillary tube, the inner diameter of the conduit can range from a few microns to about 4–5 mm. An exemplary inner diameter for a tubular conduit suitable to provide 1 uL/min flow rate under typical fluid pressures is about 320 um. Other exemplary inner diameters include about 50 um, about 75 um, about 800 um, about 1 mm, about 2 mm, and about 3.9 mm. An inner diameter of about 3.9 mm or 4.6 mm is suitable, for example, for certain conventional chromatography applications. Suitable wall thicknesesss, e.g. the difference between an inner diameter and an outer diameter include, $\frac{1}{16}$ of an inch, $\frac{1}{4}$ of an inch, and $\frac{3}{8}$ of an inch. In preferred embodiments, an inlet orifice in the housing unit is in fluid communication with a first end of the fluid separation conduit within the housing, and an outlet orifice in the housing unit is in fluid communication with a second end of the fluid separation conduit. The fluid separation conduit provides a fluid flow path within the housing from the inlet orifice to the outlet orifice. A first connector, e.g. a first ferrule-sub assembly, and a second connector, e.g. a second ferrule sub-assembly, can be fitted to the first end and the second end of the fluid separation conduit, respectively. More specifically, in embodiments comprising ferrule sub-assemblies each of the ferrule sub-assemblies comprises a ferrule or end cap seated over the end of the fluid separation conduit. The ferrule sub-assembly preferably comprises a compression ring securing the attachment to the fluid separation conduit and/or creating a fluid-tight seal between the end of the conduit and other channels or devices in fluid communication with the fluid separation conduit. The ferrule sub-assemblies, further described below, each preferably provides a seating and sealing surface for its respective fluid flow port. In preferred embodiments, the ferrule sub-assembly comprises a frit body providing the seating and sealing surface. Preferably each of the ferrule sub-assemblies is secured to the housing unit in a fixed position, optionally being removably fixed, at its respective port. In this manner, the fluid separation conduit can be conveniently anchored to the housing unit, e.g., to a component of the housing unit which is assembled with one or more other housing components after the fluid separation conduit is attached, to construct the housing unit of the conduit cartridge. In certain embodiments, a surface of the ferrule sub-assembly at the inlet end of the fluid separation conduit is a substantially flat surface having a fluid opening for the inlet port and facing substantially outwardly from the housing unit to seat and seal conveniently against a corresponding surface of a fluid feed line or other fluid source feeding fluid to the fluid separation conduit cartridge for testing, analysis, etc. Similarly, a surface of the ferrule sub-assembly attached to the outlet end of the fluid separation conduit provides a substantially flat surface having a fluid opening for the outlet port and facing substantially outwardly from the housing to seat and seal conveniently against a corresponding surface of a fluid return or waste line or other fluid receiving device for accepting fluid from the fluid separation conduit cartridge after it has been tested, analyzed or subjected to other operation(s) by the fluid separation conduit within the housing. It should be recognized that the designation of a port of the housing unit as being an inlet port or an outlet port may in certain instances be arbitrary and merely a matter of convenience or choice, such as where the conduit cartridge is usable in either direction, preferably then being side-to-side symmetrical so that it can be properly installed in either orientation. In other embodiments, an outwardly extending connector is provided on a fluid separation conduit cartridge to enable insertion of the conduit cartridge fluid ports into wells or receiving sockets of a manifold or mounting device or the like, for fluid connection and sealing. As discussed above, the housing unit may comprise innumerable other devices positioned within or attached to the housing unit and or components thereof, e.g. the fluid separation conduit, the memory unit, the ferrule subassemblies, etc.

In accordance with an additional aspect, the fluid separation conduit cartridge disclosed here can be used to separate one or more species in a fluid. As used here, separate, separation, or fluid separation refers to resolving two or more species in the fluid. Preferably, baseline separation, e.g. baseline resolution, is achieved using the conduit cartridge disclosed here to provide for accurate quantitative measurements of the species in the fluid. The fluid separation conduit of the conduit cartridge disclosed here may take numerous forms, e.g. cylindrical, serpentine, coiled, and the like, and preferably contains one or more types of fluid separation media (also referred to below as a stationary phase(s)) for separating species in a fluid. As used here stationary phase refers to the material(s) coated, adsorbed, absorbed, or attached to the inner surfaces of the fluid separation conduit, e.g. the surfaces of the fluid separation conduit that are contacted by fluid from a fluid reservoir, for example. The stationary phase is operative to adsorb and to allow for desorption of species in the fluid, e.g. allows for reversible adsorption of species in the fluid. Based on the differential solubilities of the species in the fluid and in the stationary phase, the stationary phase acts to separate the species in the fluid. As used here differential solubilities refers to the solubility of a species in the stationary phase and in a fluid passing over or through the stationary phase, e.g. the mobile or fluid phase. For example, if a given species is more soluble in the stationary phase than in the fluid phase, then the given species remains adsorbed to the fluid separation conduit and does not elute. However, when the species becomes more soluble in the fluid phase than in the stationary phase, e.g. by altering the composition of the fluid phase using a solvent gradient, for example, the species is desorbed from the stationary phase and elutes from the fluid separation conduit, e.g. flows out of the cartridge in the fluid phase. Because different species have different solubilities in the different phases, e.g. partition differently between the stationary and fluid phases, depending on the selected nature of the stationary phase and the fluids, separation of the species in a fluid can be achieved. The nature of the stationary phases may vary depending on the intended use of the fluid separation conduit cartridge. For example, C18 phases may be used for separation of generally nonpolar species in a fluid while strong anion exchangers (SAX) might be used for separation of charged species in a fluid. One skilled in the art given the benefit of this disclosure will be able to select suitable stationary phases for an intended use. Preferably the stationary phase is selected from materials having nonpolar functional groups, e.g. C18 and the like, materials with negatively charged functional groups, e.g. $R_1$—$SO_3^-$ groups, $R_1$—$COO^-$ groups and the like, and materials with positively charged functional groups, e.g. $R_2$—$NH_3^+$ groups and the like, where $R_1$ and $R_2$ may be any group linked to the $SO_3^-$/$COO^-$ and $NH_3^+$ moieties respectively. Depending on the nature of the stationary phases, suitable fluid phases may be chosen such that the species in a fluid will elute at different times, e.g. the species will have different retention times. One skilled in the art given the benefit of this disclosure will be able to select suitable fluid phases for separating one or more species in a fluid. In preferred embodiments, a solvent gradient is used to separate the species in a fluid. As used here solvent gradient refers to changing the composition of the fluid phase with increasing time. Suitable solvent gradient methods will be apparent to those skilled in the art given the benefit of this disclosure and exemplary solvent gradient methods are discussed below.

In accordance with another aspect, the conduit cartridges typically are in fluid communication with one or more devices operative to move fluid into and/or out of the fluid separation conduit cartridge. That is, one or more devices, in fluid communication, with the conduit cartridges are operative to generate a fluid flow such that species introduced into the fluid flow can enter into the conduit cartridge, be separated by the conduit cartridge, and/or subsequently flow out of the conduit cartridge. Suitable devices for generating a fluid flow are well known to those skilled in the art and include but are not limited to pumps, e.g. piston pumps, standard HPLC pumps and the like, vacuum manifolds, and the like. Those skilled in the art will recognize that these devices are useful in controlling the flow rate of species out of the conduit cartridge, e.g. are used to alter the retention times of the species, and thus can effect separation of the species. For example, lower fluid flow rates can be used to provide for better separation of the species, whereas higher fluid flow rates may be used to elute the species from the conduit cartridge more rapidly. One skilled in the art given the benefit of this disclosure will be able to select numerous devices for generating a fluid flow. Suitable devices may also be in fluid communication with one or more sample introduction devices, such as those described in detail below, e.g. fixed-loop injectors, auto-injectors, auto-samplers, and the like.

It will be recognized by those skilled in the art, given the benefit of this disclosure, that the fluid separation conduit cartridge disclosed above may include numerous other components. For example, additional columns, e.g. one or more guard columns, might be in fluid communication with the fluid separation conduit. Additional memory units, such as those discussed above, may be included in the conduit cartridge. Identifiers, such as RF tags, bar codes and the like may be placed on or in the housing unit of the cartridge. Additional connectors, e.g. electronic connectors such as, for example, PCMCIA connectors, serial connectors, parallel connectors, USB connectors and the like, may be positioned on any surface of the housing unit and optionally may be in electrical communication with one or more memory units. Such additional devices may be incorporated into the conduit cartridge in any of numerous manners, e.g. incorporated inside the housing unit of the conduit cartridge or may be removably attached to one or more outer surfaces of the housing unit. It will also be recognized by those skilled in the art, given the benefit of this disclosure, that the fluid separation conduit cartridges disclosed above may omit one or more of the components described above, e.g. a memory unit and/or a connector may be omitted. That is, in certain embodiments, the memory unit, for example, is omitted from the conduit cartridge disclosed above. Thus, in certain embodiments, the conduit cartridge may comprise a housing unit and one or more connectors but no memory unit. In other embodiments, the conduit cartridge may comprise a housing unit and a memory unit but no connectors. One skilled in the art, given the benefit of this disclosure will be able to design conduit cartridges with selected components suitable for an intended use.

In accordance with additional aspects, a fluid separation conduit cartridge comprising at least a housing unit and a separation conduit that is potted is disclosed. As used here potted refers to surrounding, e.g. enveloping, encasing, enclosing, and the like, one or more components of the cartridge with a potting compound. The potting compound prevents movement of the components within the conduit cartridge and provides protection to any sensitive components, e.g. a memory unit, within the cartridge. In certain embodiments, the potting compound envelops the conduit cartridge and allows the cartridge to withstand higher pressures without rupturing, fracturing or leaking. Exemplary potting compounds include but are not limited to thermoset and thermoplastic polymers, e.g., epoxies, glass filled epoxies, metal filled epoxies, carbon-filled epoxies, and the like. In certain embodiments, the fluid separation conduit cartridge may comprise a housing unit, one or more memory units, one or more connectors, and a potted fluid separation conduit. The potting compounds typically have no effect on the memory unit or any other components within the housing unit or attached to the housing unit. That is, the memory unit may be integrated into the housing unit of the cartridge and the potting compounds can be disposed in the housing unit to encapsulate the fluid separation conduit and the memory unit without adversely affecting operation of the conduit cartridge. The potting compound can be disposed prior to packing the conduit with a packing material or after packing the conduit with a packing material. In certain embodiments, the conduit cartridge comprises a housing unit, one or more connectors, a potted conduit, and a memory unit. In yet other embodiments, the conduit cartridge comprises a housing unit, one or more connectors and a potted conduit but no memory unit. One skilled in the art, given the benefit of this disclosure, will be able to choose components for incorporation into the conduit cartridges disclosed here suitable for an intended use.

In accordance with a method aspect, a method for making a fluid separation conduit cartridge comprising a fluid separation conduit and at least one memory unit is disclosed. An assembled cartridge is provided comprising all of the necessary elements for a fluid separation conduit including at least one memory unit. The fluid separation conduit and any other internal components, e.g. the memory unit, may optionally be potted as discussed above. The memory unit can then be programmed at the manufacturing facility. The cartridge can then be loaded or packed with a suitable packing material, e.g. a suitable stationary phase, based on the intended use of the fluid separation conduit cartridge. Numerous methods for loading stationary phases are well known to those skilled in the art and include, for example, flowing a slurry of a packing material into the conduit using a high pressure pump. Following the loading of the conduit with a suitable stationary phase, the cartridge can undergo testing for quality assurance at the manufacturing facility the results of which may then be incorporated into the memory unit. Following use by an end-user, the cartridge can intermittently, e.g. daily, weekly, monthly, etc., throughout its lifetime be examined for quality control issues, for example, in the process of validation of a particular chromatographic method. The cartridge can be tested at a test site, for example, within an end-user's facility, the results of which may be incorporated into the memory unit.

In accordance with an additional method aspect, a method for making a fluid separation conduit cartridge comprising a fluid separation conduit that is potted is disclosed. An assembled fluid separation conduit cartridge is provided, comprising at least a housing unit, and one or more potting compounds are disposed within, or optionally on or around, the conduit cartridge. The potting compounds may be disposed using numerous methods known to those skilled in the art including but not limited to injection of the potting compound using a syringe and needle. In certain embodiments, one or more of the cartridge faces on the housing unit are removed, or not assembled, and the potting compound is poured or injected into the housing unit in a sufficient amount to envelop at least a portion or all surfaces of the fluid separation conduit, more preferably enveloping substantially all surfaces, e.g. outer surfaces, of the fluid separation conduit that are located internally within the housing unit. In other embodiments, the potting compound is disposed in the conduit cartridge prior to, or simultaneously with, insertion of a fluid separation conduit into the housing unit. The cartridge can then be packed with a suitable packing material, e.g. a suitable stationary phase, based on the intended use of the fluid separation conduit cartridge. Numerous methods for loading stationary phases are well known to those skilled in the art and include, for example, those mentioned here. Following the packing of the cartridge, the cartridge can undergo testing for quality assurance at the manufacturing facility, e.g. testing to assess cartridge quality and operation at high pressures. In accordance with another aspect, a fluid separation conduit cartridge comprises at least a housing unit, a fluid separation conduit within the housing unit, an inlet orifice in fluid communication with a first end of the fluid separation conduit, and an encryption device. As used here, an encryption device is any device which is operative, either alone or in combination with other devices or components elsewhere, to perform an encryption operation on information, e.g. a signal containing or corresponding to a method, e.g. an LC method, to be performed by the cartridge and/or other components of a system comprising the cartridge, or a signal containing or corresponding to test results obtained by the cartridge or a system comprising the cartridge, e.g. test results from a detector in fluid communication with the cartridge, etc. Thus, information, as used here, can include but is not limited to data that is acquired by a cartridge, data that is acquired by an instrument, data that is acquired by an analytical system, methods that are used by an instrument, system or a conduit cartridge, messages that are sent from a conduit cartridge to a system, e.g. an instrument, or from a system to a conduit cartridge, methods or data that are sent from a conduit cartridge to a remote operating facility, methods or data that are sent from a operating facility to a remote conduit cartridge, quality control and assurance protocols used by an instrument or a conduit cartridge, corporate trade secrets, manufacturing protocols, manufacturing records, records of cartridge use, and any other parameters or data that a conduit cartridge might use or need for chemical, biological, biochemical, or environmental analyses and separations. Exemplary encryption operations performed by the encryption device include encryption, decryption, or both, such as operations to compress, to encrypt, to transmit, to receive, and/or to decrypt information. For convenience, an encryption device is in some cases below as an encrypting device; likewise reference is made below in some cases to encrypting and/or to decrypting rather than to the more generic "encryption operation" but will be understood from context to refer to the more generic concept.

As used here, remote or remotely means a conduit cartridge and an operating facility that are located at some distance from each other, e.g. in separate buildings, environments, and the like. Remote or remotely also means that the conduit cartridge may be connected by a wire to an operating facility, but input of information occurs by sending the information from the operating facility through the wire and to the conduit cartridge. Remote or remotely also means inputting of information other than by means of a keypad or input device incorporated on the conduit cartridge or instrument. Remote or remotely also means that the attachment for communication, e.g. a wire, between the conduit cartridge and an operating facility is not permanent, e.g. the wire is removably attached. Remote or remotely also means that the conduit cartridge and an operating facility may be in communication through a wireless device such as a cellular phone, RF transmitter and receiver, satellite transmitter and receiver, devices using 802.11b protocols, or comparable devices.

In accordance with another aspect, information is encrypted using any encryption method known to those skilled in the art. Preferably a strong encryption algorithm, e.g. 56-bit encryption algorithm, 128-bit encryption algorithm or higher is used. Exemplary encryption algorithms include but are not limited to Blowfish and DES, for example. In addition to encryption, there may be a need to ensure that all information used by the conduit cartridge, accessed by the conduit cartridge, or sent to the conduit cartridge can be verified. This feature prevents tampering with or altering of the information in the conduit cartridge. Because verification provides that any information sent to the conduit cartridge or obtained by the conduit cartridge will be secure, the conduit cartridge may be placed remotely for numerous analyses.

In accordance with another aspect, encryption and decryption may be performed using the memory unit described here, or may be performed using encryption devices, such as, for example, a microprocessor, a subroutine stored in a memory unit, and the like. In embodiments, comprising a microprocessor, the microprocessor can be in electrical communication with a memory unit. In other embodiments, the microprocessor comprises an internal memory store such that an additional memory unit is not required. In yet other embodiments, a subroutine for encrypting and decrypting information is resident in a memory unit, e.g. a ROM or EEPROM and is operative to encrypt and decrypt information received by, or sent by as the case may be, the conduit cartridge. Other encryption devices will be apparent to those skilled in the art given the benefit of this disclosure.

In accordance with an additional aspect, the conduit cartridge can use a two-part encryption and signing process. In the first part of the encryption process, all information on the conduit cartridge is encrypted using an encryption driver. All information that is sent to the conduit cartridge, either by an instrument or by a remote operating facility, for example, passes through the encryption driver. Similarly, all information that is sent by the cartridge, for example, either to an instrument or to a remote operating facility, passes through the encryption driver. In preferred embodiments, the encryption driver comprises an Authentication Engine, an Encryption Engine, a Signature and Verification Engine, and a Card Filing System. The Authentication Engine provides initial access to the information on the conduit cartridge. Multiple levels of access may exist including but not limited to read-only, write-only, read and write once, read and write once authorized, read and write, and restricted access. The Encryption Engine preferably uses an encryption algorithm or an encryption device that encrypts or decrypts information, such as those discussed here. Preferably, the Encryption Engine uses a strong encryption method, such as DES, Blowfish, or other strong encryption algorithms known to those skilled in the art. The keys for the encryption may also be encrypted and stored in the Encryption Engine. The keys may be decrypted when necessary for encrypting or decrypting information. The Signature and Verification Engine (SAVE) typically is a record keeping device that signs all information to ensure that a record of events exists. The SAVE typically is responsible for signing and storing all information passed to the encryption driver. The signature may be used to verify that another party did not alter information on the conduit cartridge. When information on the conduit cartridge is encrypted, a signature referring to the encrypted information may be added. The signature may be transmitted with or stored with the encrypted information. When verification of encrypted information is desired, the encrypted information that has been signed can be decrypted and compared with the information of interest. If upon comparison of the information, the information is similar, then the information has not been altered since the signature was generated. The signature may also be used to construct a record for tracking the usage history of the conduit cartridge. In certain preferred embodiments, to prevent unwanted parties from obtaining the keys that are required to decode the encrypted information or the signatures, users may validate their keys against a central key store. The SAVE can make a request to a central server to validate a public key, e.g. a request to the central server through the Internet. The SAVE can also ensure that all public keys that are required to verify the signatures of the stored and encrypted information are available.

It will be recognized by those skilled in the art that other encryption processes and algorithms may be used. That is, the two-part encryption process described above is not necessarily required to generate encrypted information. Other encryption processes and algorithms, including those which involve single or multiple steps or subroutines, can be used to encrypt and/or decrypt information suitable for transmitting to a conduit cartridge, a system, or a remote operating facility. One skilled in the art given the benefit of this disclosure will be able to select additional encryption algorithms and processes suitable for transmission of secure information to and from the conduit cartridges disclosed here.

In accordance with another aspect, a conduit cartridge capable of transmitting or sending encrypted information to a remote destination is disclosed. The device and methods used by the conduit cartridge to transmit the information include the aforementioned methods of sending the information through a modem by fax or other method, sending the information by e-mail or over the Internet, sending the information by wireless transmission using a cellular phone, devices using 802.11b protocols, or comparable devices, sending the information by RF transmission, sending the information by satellite transmission, or sending the information through a wire that links the conduit cartridge to another device or to an operating facility. Therefore, in addition to the components of the conduit cartridge described here, the conduit cartridge may optionally include other electrical and mechanical components to provide for transmission of information or other operations. In certain preferred embodiments, the information may be transmitted from the conduit cartridge to a remote operating facility using any known devices and methods for transmitting information such as e-mail, the Internet, wireless phone, fax, modem, RF transmission, satellite transmission, a direct connection between the conduit cartridge and an operating facility, such as a wire, or other similar transmission devices. Upon receipt of the information at its destination, the information may be decoded and read only by one who possesses an appropriate decoding key corresponding to the encryption key. For example, the information may be encrypted by the conduit cartridge using a customer's public key, transmitted from the conduit cartridge to the customer, and then decoded using the customer's private key. This feature provides for secure transmission of the information regardless of the methods used for transmitting the information. After successful decoding, the information can be analyzed, stored, or used for other reasons applicable to the function of the conduit cartridge.

In accordance with another aspect, information that is transmitted from a conduit cartridge to an analytical system, e.g. an instrument, in communication with the conduit cartridge may be encrypted. One skilled in the art given the benefit of this disclosure will recognize that to effectively alter the method used for testing or analysis using information stored on the conduit cartridge, as discussed here, there must be some communication between the cartridge and the system. If unsecure or unencrypted information was sent from the cartridge to the system, an unauthorized party might gain access to trade secrets or proprietary corporate secrets contained in the information. Therefore, information sent from the conduit cartridge to a system, in communication with the conduit cartridge, may be encrypted using the system's public key, for example. Upon arrival at the system, the encrypted information may be decrypted using the system's private key. Therefore, the information remains encrypted during transmission from the conduit cartridge to the system. This feature provides added security during transmission of information sent from the conduit cartridge to the system.

It will be recognized by those skilled in the art that the conduit cartridges disclosed have innumerable uses. For example, one or more analytical system comprising a conduit cartridge can be placed remotely at a user's facility and any results of testing analyses can be sent to a remote operating facility. Alternatively, the results might be sent directly to a regulatory agency for monitoring of chemicals, pollutants, and the like generated by a manufacturing facility for example. That is, encrypted test results could be transmitted directly to a regulatory agency, for example, which has an appropriate key to decrypt the information. Therefore, unauthorized access, by members of the manufacturing facility for example, is prevented. Such direct transmission to a regulatory agency, for example, prevents tampering or altering of the information by the manufacturing facility.

In accordance with another aspect, a conduit cartridge capable of receiving information is disclosed. The device and methods used by the conduit cartridge to receive information include the aforementioned devices and methods of receiving the information through a modem by fax or other method, receiving the information by e-mail or over the Internet, receiving the information using a wireless device such as a cellular phone or comparable device, receiving the information using a RF receiver, receiving the information using a satellite receiver, or receiving the information through a wire that links the conduit cartridge and the operating facility. Therefore, in addition to the components of the conduit cartridge described here, the conduit cartridge may optionally contain other electrical and mechanical components to provide for reception of information or other operations. A conduit cartridge operative to receive information provides the ability to alter remotely the method used by the remote conduit cartridge or analytical system.

In accordance with another aspect, to decrease the time required for information to be transmitted and subsequently received at its destination, the conduit cartridge may use compression algorithms. Compression of information effectively allows for faster transmission of a given amount of information. The conduit cartridge may use any compression algorithm known to those skilled in the art. Additionally, any compression algorithm that generates ARC, TAR, ZIP, GZ files or other compressed file formats may be used. For example, the information might be compressed using commercially available computer software programs such as PKZip™ (PKWARE, Inc.) or WinZip™ (WinZip Computing, Inc.) or freely available programs and commands, e.g. gzip, operative to compress information. The information could then be encrypted using any method known to those skilled in the art such as, for example, public/private key encryption. Transmission of the compressed and encrypted information may occur using any known transmission device including wireless transmission devices that utilize 802.11b protocols, for example. One skilled in the art will recognize that the information may be compressed and then encrypted or may be encrypted and subsequently compressed.

In accordance with other aspects, the conduit cartridge may be directly plugged, e.g. directly interface, into a device for downloading or uploading encrypted information. As used here directly plugged means that the cartridge and the device are in direct communication preferably without any intervening wires or devices. For example, the conduit cartridge may directly interface with a computer or other electronic device to upload or download information. This interface may consist of a direct connection such as a female connector on the conduit cartridge coupled to a male connector on a computer. One skilled in the art will recognize that other types of connectors may be used to accomplish the uploading and downloading of information, e.g. PCMCIA connectors, USB connectors, serial connectors, etc. One skilled in the art will also recognize that the information on the conduit cartridge may be uploaded or downloaded using other devices such as a floppy disk or other magnetic media, through wireless transfer using infra-red transmission, 802.11b protocols or any other methods that transfer information from one source to another.

In accordance with another aspect, one or more digital IDs may be assigned to the cartridge to provide, for example, a unique identifier to the cartridge, a method associated with the cartridge, or an analytical system associated with the cartridge.

The conduit cartridge disclosed here provides useful information as to the cartridge's performance which is critical in both Good Manufacturing Practice and Good Laboratory Practice settings. Damaged cartridges can be detected early, thereby saving on both frustration and useless data acquisition. Full traceability of the cartridge throughout its lifetime is available to the end-user or any other interested party with appropriate access capabilities.

BRIEF DESCRIPTION OF THE FIGURES

Certain preferred embodiments of the present invention will be described below with reference to the accompanying figures in which.

It will be recognized by those skilled in the art that the fluid separation conduit cartridges disclosed in the figures are not necessarily to scale. The dimensions of the cartridges may have been enlarged, relative to the dimensions of an analytical system, e.g. a chromatography system, an instrument and the like, for example, for ease of illustration and for clarity of viewing. Those skilled in the art given the benefit of this disclosure will recognize that the conduit cartridges may have any dimensions suitable for interfacing with an instrument, for example.

DETAILED DESCRIPTION OF CERTAIN PREFERRED EMBODIMENTS

It will be recognized by those skilled in the art that embodiments of the fluid separation conduit cartridge described here may be used for numerous fluid separation methods including but not limited to liquid chromatography (LC), high performance liquid chromatography (HPLC), fast performance liquid chromatography (FPLC), supercritical fluid (SCF) chromatography, gas chromatography (GC), capillary liquid chromatography, capillary electrophoresis, other liquid-phased separation techniques, e.g micellular electrokinetic chromatography (MEKC), isoelectric focusing, isotachophoresis and other chromatographic methods commonly used by those skilled in the art. For convenience and not intending to limit the fluid separation conduit cartridge in any manner, the detailed description of certain preferred embodiments described here is directed to fluid separation conduit cartridges operative to be used in liquid chromatography. However, one skilled in the art, given the benefit of this disclosure will be able to design and use the fluid separation conduit cartridges disclosed here for these and other uses.

Figure 1:
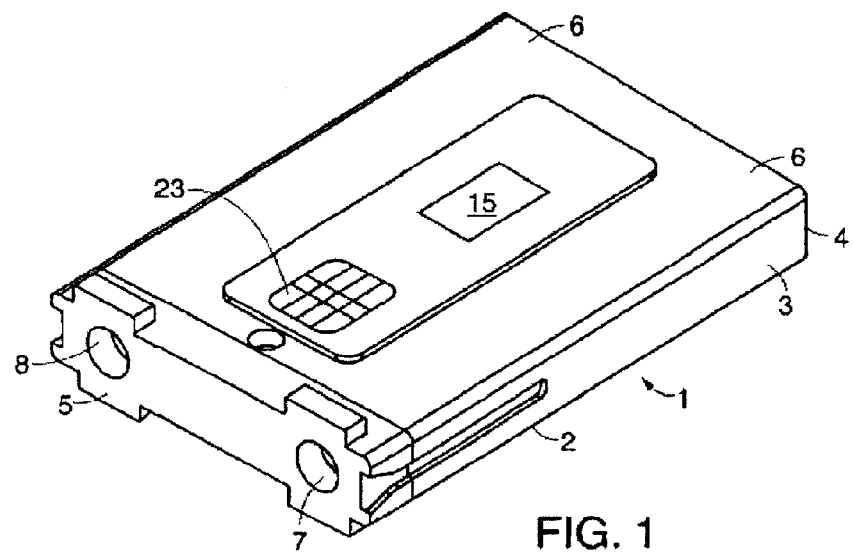
FIG. 1 is a perspective view of a fluid separation conduit cartridge, in accordance with preferred embodiments.
Figure 2:
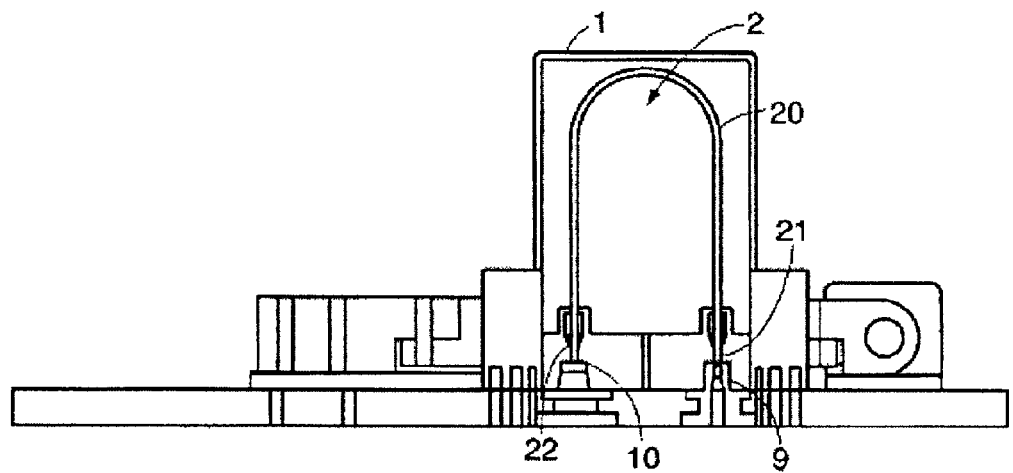
FIG. 2 is a cut-away view of the fluid separation conduit cartridge shown in FIG. 1, in accordance with preferred embodiments.

In accordance with certain preferred embodiments, a fluid separation conduit cartridge comprises an exterior portion and an interior portion. Referring to FIG. 1, the exterior portion is defined by a housing unit 1 which comprises a base plate 2, at least two side plates 3, a rear manifold 4 which is perpendicular to the two side plates, a front manifold 5 that lies perpendicular to the two side plates, and a cover plate 6. An input orifice 7 and an output 8 orifice are shown. Both the input orifice 7 and output orifice 8 are disposed within the front manifold 5. The dimensions of the housing unit, e.g. the cartridge's footprint, can vary depending on the intended use of the cartridge and upon the instrument or device to which the cartridge is intended to interface. For example, in certain embodiments the cartridge is about 1¾ inch, more typically about 3–4 inches wide by about 1¾ inches, more typically 4¾ to about 19 inches. The 19 inch dimension is a standard rack dimension and, accordingly, cartridges as disclosed here, in certain embodiments have one dimension equal to 19 inches or ½ that size or other standard fraction of that full rack dimension. The thickness or height of the cartridge will follow somewhat the footprint dimensions and typically will be at least about ⅝ of an inch or more. The cartridge, for example, may have the dimensions of a postage stamp, a PCMCIA card (especially a Type III PCMCIA card), a credit card, or the like. The thickness of the cartridge can also vary depending on the intended use of the cartridge. One skilled in the art given the benefit of this disclosure will be able to select suitable thicknesses for accommodating suitable components into the conduit cartridge and to provide the proper dimensions for interfacing the conduit cartridge with an instrument, analytical system, e.g. a chromatography system, and the like. Referring to FIG. 2, the input orifice 7 and output orifice 8 each comprise fittings (9, 10) that can be used to facilitate entry and exit, respectively, of a fluid, with or without any dissolved species or particulate matter, through the cartridge. The fittings 9, 10 can have an outer surface aspect and an inner surface aspect. The outer (or exterior) surface aspect interfaces with an exterior connection, such as an LC separation conduit 20 for example, carrying fluid. The inner (or interior) surface aspect interfaces with the interior of the housing unit 1. The fitting is secured within an orifice by numerous devices and methods known to those skilled in the art, e.g. clamps, adhesives, welding, and the like In accordance with certain preferred embodiments and referring to FIG. 2, an LC separation conduit 20, housed within the interior of the housing unit 1, with two defined ends is attached at a first end 21 to input orifice fitting 9 and is attached at a second end 22 to output orifice fitting 10. Numerous methods suitable for attachment are well known to those skilled in the art and include, for example, snap-connectors, solvent welding, IR welding, compression fittings, adhesives and the like. Preferably, input orifice fitting 9 and output orifice fitting 10 each is coated with a substance in order to maintain a fluid-tight seal. That is, each fitting is preferably coated with a material that assists in preventing any fluid from permeating between the junction formed by an orifice fitting and surface of the manifold. Examples of such materials include but are not limited to polytetrafluoroethylene, e.g. Teflon™ tape and Teflon™ coatings (e.g. sprayed on Teflon™ coating), and other polymer materials such as polyethylene, PEEK coatings, PCTFE (e.g. KEL-F™), and the like. In preferred embodiments, a capillary conduit, e.g. a capillary column, is used in the conduit cartridge. In certain embodiments, additives, such as carbon black, dyes, titanium dioxide, gold, e.g. electroplated gold or electrolessly plated gold, carbon particles, additional polymers, e.g. a secondary polymer or second phase polymer reactive with the primary polymer of the laminate layer, IR absorbing materials, and the like, may be included, as a surface coating and/or a body filler, in the materials used to form the column. The first end of the capillary column can interface with the inner surface aspect of the input orifice fitting (that is, the surface aspect which is interior within the housing unit), while the second end can interface with the inner surface aspect of the exit orifice fitting. The length of the capillary column in the present embodiment can range from about 6 cm to about 25 cm though longer capillary columns may be used by coiling the column within the housing unit. The rear manifold 4 and front manifold 5 can be positioned and secured into place with the remaining housing unit 1 by methods and devices well known to those skilled in the art. Suitable methods and devices for securing the manifolds to the housing unit include but are not limited to employing an adhesive agent, a screw forming a male unit which is then placed in apposition with a female union, a preformed male connector placed in apposition with a female union, and the like.

In accordance with certain preferred embodiments, the conduit cartridges disclosed here are typically in fluid communication with one or more devices operative to generate a fluid flow. The fluid typically comprises a buffer or solvent and any dissolved analytes or species, as discussed above. In preferred embodiments, a plurality of devices for generating a fluid flow are used such that solvent gradients may be implemented to achieve better, and more efficient, separations between the species in the fluid. The choice of devices typically depends on the amount of solvent to be moved within a period. That is, the choice of devices for generating a fluid flow typically depends on the desired flow rate necessary to achieve separation of the species. For example, in preferred embodiments, one or more pumps are in fluid communication with the conduit cartridge, and optionally with one or more injectors, e.g. fixed-loop injectors, auto-injectors, auto-samplers, and the like, for introducing samples into the fluid flow. Suitable pumps include but are not limited micro-pumps, which typically can generate a fluid flow rate between about 30 uL/min and about 100 uL/min, analytical pumps, which typically can generate a fluid flow rate between about 1 uL/min to about 10 mL/min, semi-preparative pumps, which typically can generate a fluid flow rate up to about 20 mL/min, and preparative pumps, which typically can generate a fluid flow rate up to about 50 mL/min. Numerous other pumps are commercially available from manufacturers such as Waters, Inc. and Jasco, Inc. When switched on, the pumps draw fluid from solvent or buffer reservoirs and force fluid through the remainder of the fluid circuit, e.g. force fluid into the conduit cartridge. Any species in the fluid can be separated using the conduit cartridge, as discussed above. Depending on the solvent(s) chosen for the method, the species elute, e.g. exit the conduit cartridge, based on their differential solubilities in the fluid phase and the stationary phase. As discussed above, it is preferred that solvent gradients are used to facilitate rapid separation of the species. As used here, solvent gradient refers to varying the composition of the fluid phase with time. That is, during the separation run, e.g. the method, the composition of the fluid phase is altered such that at specified intervals during the separation run, the composition of the solvent is altered. For example, if initially, e.g. when the sample is introduced into the conduit cartridge, the fluid phase comprises 80% solvent A and 20% solvent B, then during the separation run, the composition of the fluid phase may be altered such that at a specified interval, e.g. 5 minutes after the starting the separation run, the composition of the fluid phase is 60% A and 40% B. Such alterations can be achieved in a linear fashion, a step-wise fashion, or other commonly used parameters for generating and designing solvent gradients known to those skilled in the art. One skilled in the art given the benefit of this disclosure will be able to select suitable devices for generating a fluid flow and suitable solvents and flow rate for achieving separation of species in a fluid sample.

In accordance with certain preferred embodiments, the external portion, and/or the internal portion as the case may be, of the cartridge may comprise at least one electrical connector (not shown). That is, an electrical connector may be positioned on any external and/or internal surface of the housing unit of the cartridge. Preferably, the front manifold comprises an electrical connector. Suitable electrical connectors include power and communication connectors, e.g. AC or DC power connectors, electrical leads, PCMCIA connectors, PCI connectors, serial connectors, parallel connectors, USB connectors, firewire connectors, optical and fiber-optical connectors, coaxial connectors, BCN connectors, SCSI connectors, ribbon connectors, RS-232 interfaces, and the like. One skilled in the art given the benefit of this disclosure will be able to select electrical connectors suitable for operation of the conduit cartridges disclosed here. The conduit cartridges may also include numerous other connectors, e.g. fluid connectors, as discussed in detail below.

Figure 3:
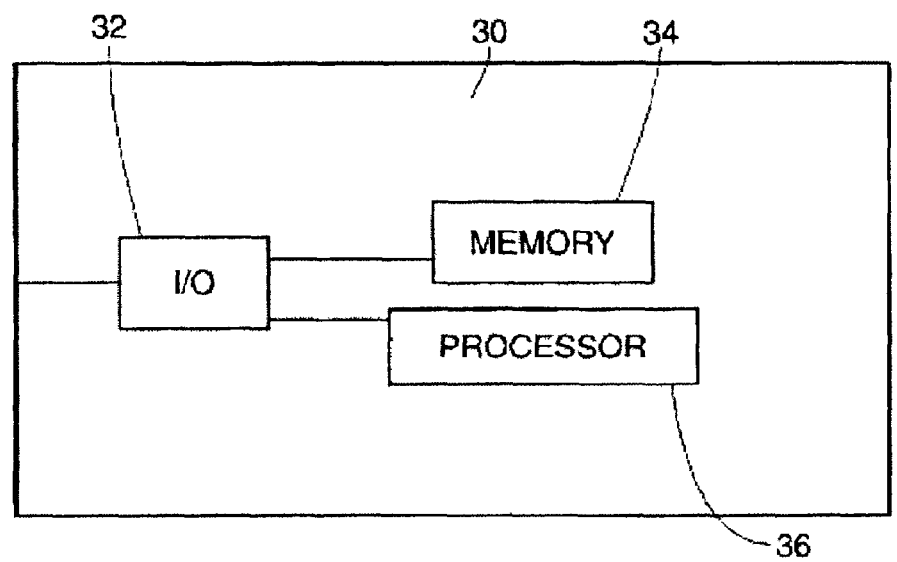
FIG. 3 is a block diagram of a circuit board contained within the housing of a fluid separation conduit cartridge, in accordance with preferred embodiments.

In accordance with certain preferred embodiments, a fluid separation conduit cartridge comprises a housing unit and at least one memory unit. The memory unit of the conduit cartridges disclosed here is suitable for use in embodiments comprising the potted conduit and also in embodiments where the conduit is not potted. That is, the memory unit may be incorporated into conduit cartridges where the conduit is potted, e.g. either inside the housing unit or outside the housing unit, and the memory unit itself may be potted without adversely affecting operation of the memory unit. For example, referring to FIG. 3, the conduit cartridge may comprise at least one read-write memory unit 30. Examples of different types of suitable memory units are well known to those skilled in the art, e.g. a Dallas Semiconductor chip DS1994 4K-Bit Plus Time Touch Memory. Suitable memory units typically include at least an Input/Output portion 32 along with memory 34 and optionally may include a processor 36, e.g. a microprocessor.

In accordance with certain preferred embodiments, the conduit cartridge preferably comprises at least two types of memory units. A first memory unit is chosen such that it is compatible with a specific analytical system. That is, the first memory unit is chosen such that is designed to interface with a specific manufacturer's analytical system, e.g. commercially available HPLC systems and the like. Preferably, the first memory unit is readable and writeable. The read-only area may include, for example, full cartridge manufacturing, quality control test data, and any other data and parameters deemed necessary by the manufacturer. The writeable area can comprise a history of cartridge usage, for example, number of injections, maximum used pressure, maximum used flow rate, pressure/flow profile, maximum temperature, as well as other features. When the conduit cartridge comprising a memory unit is placed in a particular analytical system, e.g. a chromatography instrument, the conduit cartridge details are read into the analytical system and the analytical system sets-up according to the method contained within the memory unit of the conduit cartridge. This feature allows for non-expert operators to perform an analysis without having detailed knowledge of information required to program the analytical system. On completion of the analysis, the cartridge's usage information, for example, flow rate, pressure, analysis method, number of injections, last calibration run date and reference, last used date and the like, can be updated and encoded into the memory unit. A second memory unit is chosen such that it is operative in any analytical system. The second memory unit preferably is a read-only memory unit and is supplied with a device to read the memory unit and output information in via, for example, a PCMCIA interface. The information in the second memory unit can include cartridge manufacturing, quality control test data, and other data or information relevant to the manufacturing and testing of the conduit cartridge. In general, the types of information that can be stored into the memory units include all parameters that describe the cartridge geometry and construction; also, all parameters that describe any packings, coatings or accessory chemistries, such as, filters and guard columns. Time stamp information can also be encoded into the memory unit. This information can be stored at the time the cartridge is manufactured. Additional information that can be stored is related to, for example, the method to be employed by the fluid separation conduit cartridge. Each fluid separation conduit cartridge typically is designed for a given application and dedicated to that use for the life of a particular conduit cartridge. Other information that can be stored on the memory units includes standard overall separation parameters, such as run time, data acquisition, and sampling rate. Also, the names and expected retention times and retention time windows for any targets and/or expected analytes which will be eluted from the cartridge during the separation run can be stored in the memory unit. One skilled in the art given the benefit of this disclosure will be able to select information for storing in the memory units of the conduit cartridges disclosed here.

In accordance with certain preferred embodiments, throughout the lifetime of the fluid separation conduit cartridge, quality control information can be stored in the memory unit to provide for continuous validation of the conduit cartridge, e.g. to provide quality control measures to ensure that the conduit cartridge is operating properly. For example, the number of injections, maximum used pressure, maximum used flow rate, pressure/flow profile, maximum temperature, etc., can be stored within the memory unit. This information can be later accessed by a test center or at the manufacturing facility. Performance status can also be measured by subsequent testing of the cartridge's ability to facilitate separation of test analytes. The results can be compared to the test analysis performed at the manufacturing facility prior to delivery of the fluid separation conduit cartridge to an end-user. This capability allows for lifetime validation of the cartridge. Potentially the cartridge may be passed along to several end-users, however, the data stored within the memory unit will remain with the conduit cartridge.

In accordance with certain preferred embodiments, as disclosed above, ferrule assemblies can be employed as fittings on the ends of the fluid separation conduit cartridge. The ferrule assemblies are received into correspondingly sized sockets in the housing unit, preferably with a friction fit or, alternatively, with a snap-fit, with adhesive or other materials and devices to form a permanent or removably fixed connection between the ferrule and the housing unit. The ferrule fittings in this way serve to anchor the ends of the fluid separation conduit to the housing unit of the conduit cartridge. Preferably, the ferrule fittings are received into an end plate of the housing unit, with the two ends of the fluid separation conduit extending back through the end plate into the interior of the housing unit formed by an open-ended concave housing member attached to, and closed by, the end plate. The ferrule assemblies advantageously provide an externally facing seating and sealing surface for fluid flow into or out of the fluid separation conduit. Preferably, the ferrule is in the form of a cap, preferably being formed of metal or other suitable material. An annular wall extending from an end wall of the ferrule forms a socket into which the end of the fluid separation conduit is inserted. Preferably the ferrule socket forms a tight fit with the fluid separation conduit. A compression ring seats around the exterior of the annular wall. The compression ring, as its name suggests, is sized to compress the ferrule socket on the end of the conduit to secure it in position. Preferably the end of the annular wall is beveled or chamfered to ease its insertion into the compression ring. The compression ring typically has a somewhat conical inside wall, larger toward the end wall of ferrule, such that its fit around the annular wall of the ferrule gets tighter as it is forced on. The ferrule has a fluid flow passage extending through the end wall, whereby fluid can flow to or from the fluid separation conduit through the end wall. The ferrule sub-assembly further comprises a frit body at the exterior surface of the end wall to provide a seating and sealing surface. The frit body is seated in a well in the exterior face of the ferrule over the end of the fluid flow passage, optionally standing slightly proud of the exterior face of the ferrule, to serve as a seating and sealing surface. In use, a fluid delivery line or fluid removal line mated to the conduit cartridge to establish delivery and removal of fluid to be tested by the conduit cartridge, can be pressed against the frit body to establish a fluid-tight seal with a sufficient degree of give or resiliency to accommodate manufacturing tolerances, dissimilar temperature expansion coefficients and the like.

In accordance with certain preferred embodiments, the materials used to construct the ferrule assemblies, conduits, and other connectors of the conduit cartridge may be altered and/or reinforced to withstand high pressures depending on the intended use of the conduit cartridge. For example, stainless steels and metal plates can be used to reinforce the housing unit of the conduit cartridge. In certain embodiments, a multi-laminate structure can be included to provide increased strength for withstanding high pressures achieved using high flow rates. One skilled in the art given the benefit of this disclosure will be able to select suitable materials for forming the connectors of the conduit cartridge disclosed here including but not limited to stainless steel, PEEK, reinforced PEEK, brass, ceramics, ceramic composites, etc. Other suitable materials will be readily apparent to those skilled in the art given the benefit of this disclosure.

Figure 4:
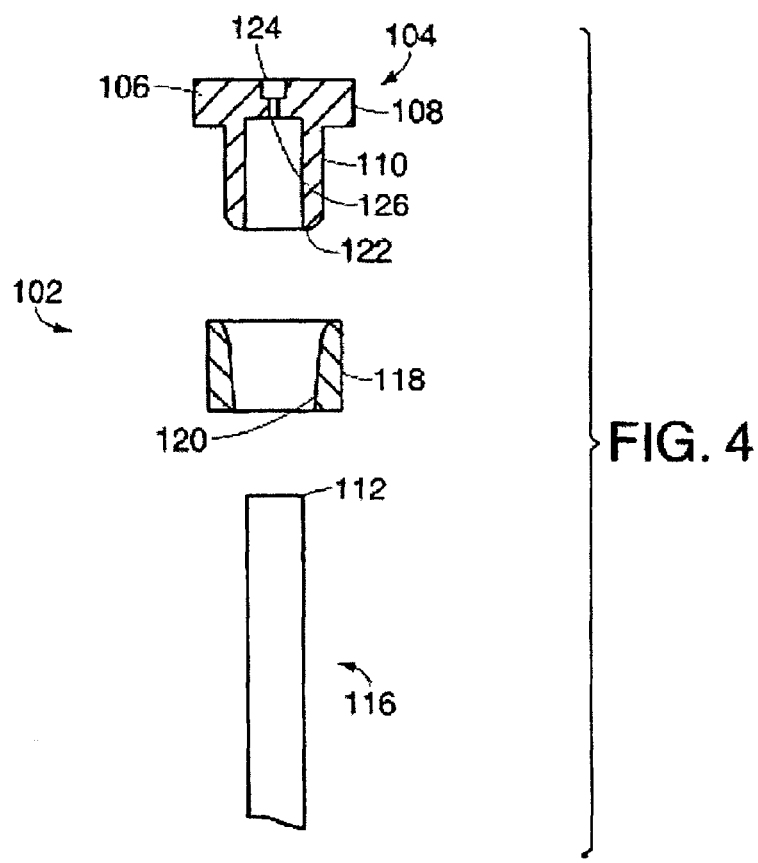
FIG. 4 is an exploded section view of a ferrule sub-assembly, in accordance with preferred embodiments.
Figure 5A:
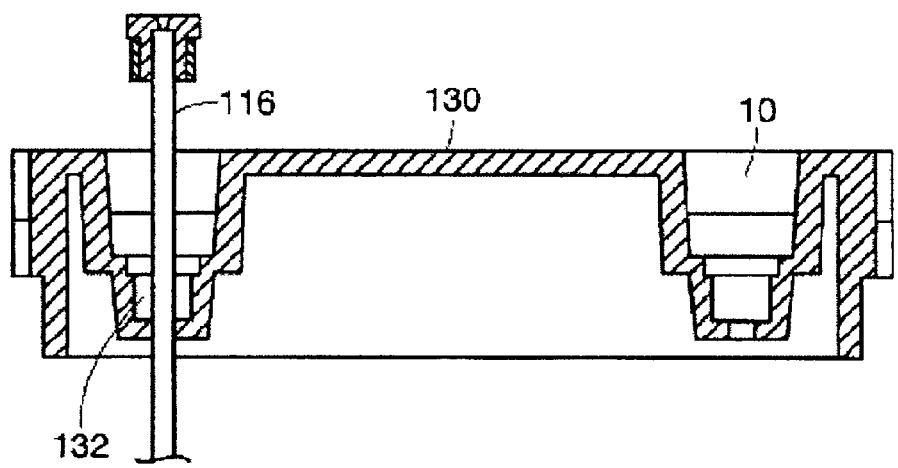
FIGS. 5a and 5b are schematic section views, partially broken away, showing the ferrule sub-assembly of FIG. 4, in accordance with preferred embodiments.
Figure 5B:
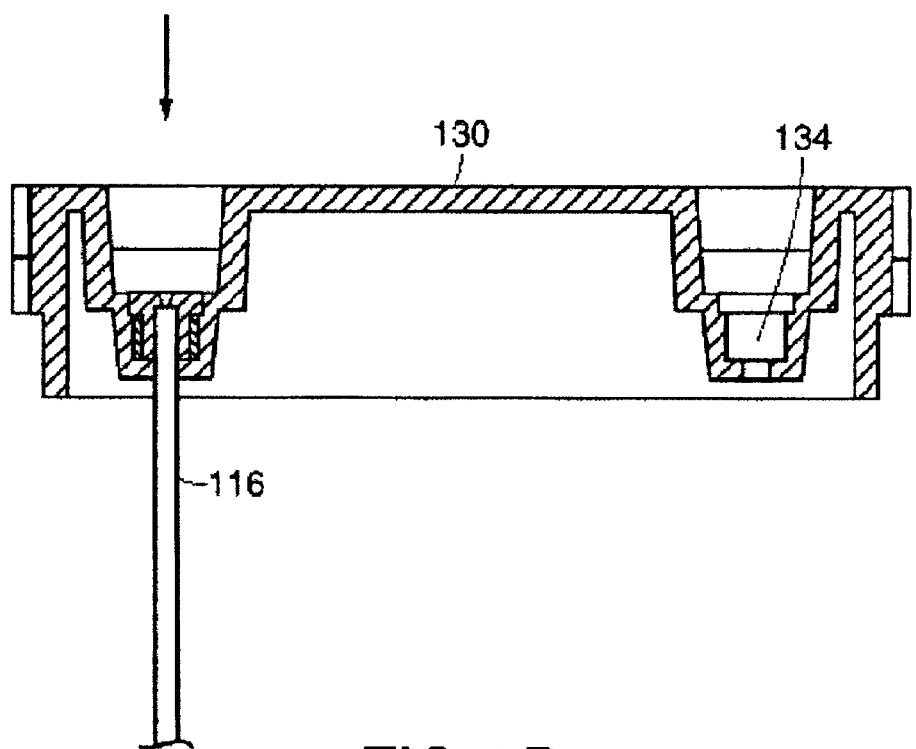

In accordance with certain preferred embodiments, referring now to FIG. 4, a ferrule sub-assembly 102 shown in exploded view is seen to comprise a ferrule 104 having an end wall 106 with an exterior surface 108 and an annular wall 110 forming a ferrule socket to receive a first end 112 of a fluid separation conduit 116. While the drawings are not necessarily to scale, inside surface 114 of annular wall 110 is sized to form a friction fit, or other tight fit, with the exterior surface of the first end 112 of the fluid separation conduit 116. Compression ring 118, preferably being formed of stainless steel or other suitable material, has a slightly conical inside surface 120. The beveled end 122 of annular wall 110 eases insertion of the annular wall into the compression ring. Fitting the compression ring onto annular wall 110 tightens the fit around the fluid separation conduit. Frit body 124 is seated in well 126 in the exterior surface 108 of end wall 106 of the ferrule 104. The frit body stands slightly proud of the exterior surface 108, that is, it extends beyond exterior wall 108 slightly. Referring now to FIGS. 5a and 5b, a ferrule sub-assembly 102 as described above is seated on fluid separation conduit 116 that extends through end plate 130 of a housing unit of a conduit cartridge. It can be seen that socket 132 in end wall 130 will receive ferrule sub-assembly 102. Typically, the assembled structure shown in FIG. 5a is pressed into socket 132 using any suitable mechanical device, e.g. mechanical press, and/or pulled in by the fluid separation conduit. The result is shown in FIG. 5b, wherein the ferrule sub-assembly is seated in socket 132 and fluid separation conduit 116 extends rearwardly into the housing unit of the conduit cartridge. While, for simplicity of illustration, the second end of fluid separation conduit 116 is not shown, it will be readily understood by those skilled in the art that a ferrule sub-assembly similar to or the same as sub-assembly 102 described above can be fitted to the second end of the fluid separation conduit and seated in socket 134 of the end wall 130 of the housing unit.

In accordance with certain preferred embodiments, the components disclosed above, e.g. the connectors and memory units, may be incorporated into conduit cartridges where the conduit is potted. That is, a fluid separation conduit cartridge may comprise a potted conduit, one or more memory units, and one or more connectors. The fluid separation conduit cartridges may also comprise a display unit, such as a liquid crystal display unit 15 shown in FIG. 1, inserted within or atop an outer surface of the housing unit, such as the cover plate 6. This display unit 15 may be connected to a memory unit located within the housing unit 1. The display unit can display information stored in the memory unit, such that certain information, e.g. date of cartridge packing, may be discovered without interfacing the conduit cartridge to an instrument or other device. Any number of numerous other components may also be included in the conduit cartridges disclosed here.

Figure 7:
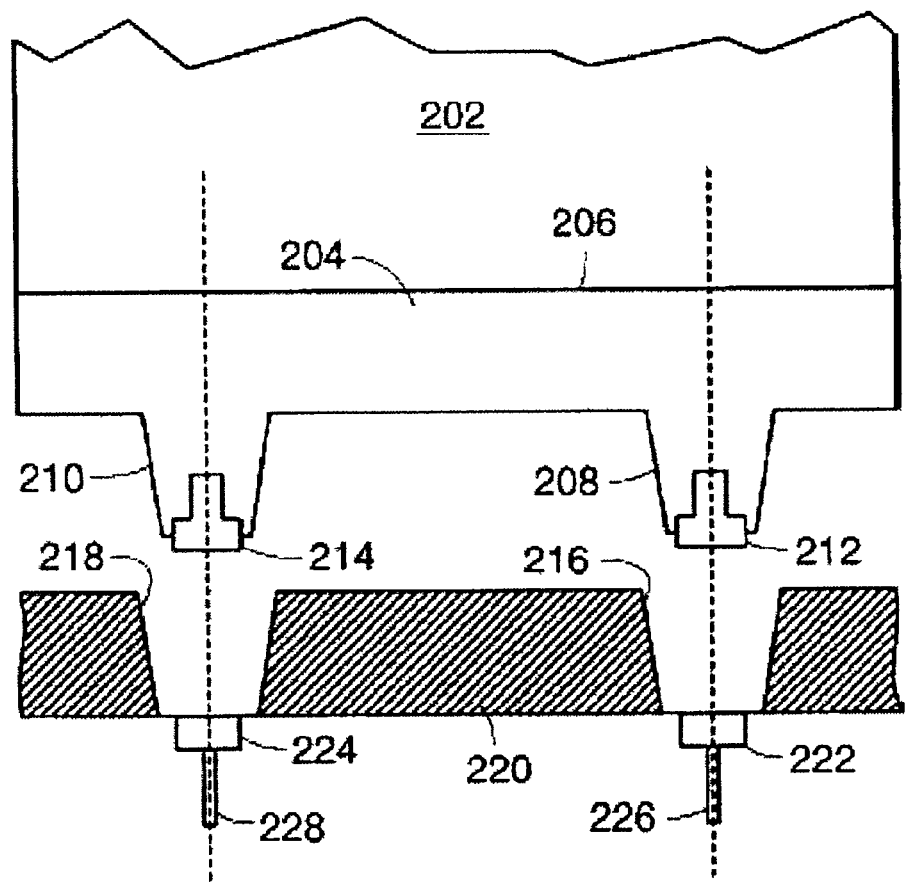
FIG. 7 is an exploded schematic view, partially broken away, showing a cartridge comprising ferrule sub-assemblies in accordance with FIG. 4 mounted in fluid ports extending outwardly from an end cap or manifold of the housing unit of the conduit cartridge, in accordance with preferred embodiments.

In accordance with certain preferred embodiments, FIG. 7 shows an additional embodiment of a fluid separation conduit cartridge. A housing unit of a conduit cartridge comprises an endplate 204 secured at interface 206 to an open-ended concave housing component 202. A fluid separation conduit (not shown) is located within the housing component 202. The first end of the fluid separation conduit terminates at a ferrule sub-assembly 212, as described above. The second end of the fluid separation conduit terminates at ferrule sub-assembly 214. Thus, ferrule sub-assembly 212 forms an inlet orifice and ferrule sub-assembly 214 forms an outlet orifice for the conduit cartridge. The inlet orifice is located in an outwardly extending projection 208 of the endplate 204. The fluid separation conduit extends rearwardly (or upwardly as shown in FIG. 7) through the endplate 204 into the housing chamber formed by housing component 202. Similarly, the outlet orifice formed by ferrule sub-assembly 214 is located in an outwardly extending projection 210 of the endplate 204, and the second end of the fluid separation conduit passes through endplate 204 to ferrule sub-assembly 214 at the outward end of projection 210. The first outwardly extending projection 208 and the second outwardly extending projection 210 each is substantially frustro-conical and symmetrical about the axis of the inlet and outlet orifices, respectively. Preferably the housing unit is generally planar, having its smallest dimension into the plane of the paper as viewed in FIG. 7. The outwardly extending projections preferably are substantially symmetrical and parallel projecting generally in the plane of the housing unit. One skilled in the art given the benefit of this disclosure will be able to use these and other suitable connectors for connecting the conduit cartridges disclosed here to suitable devices, such as analytical instruments, for example.

Figure 8:
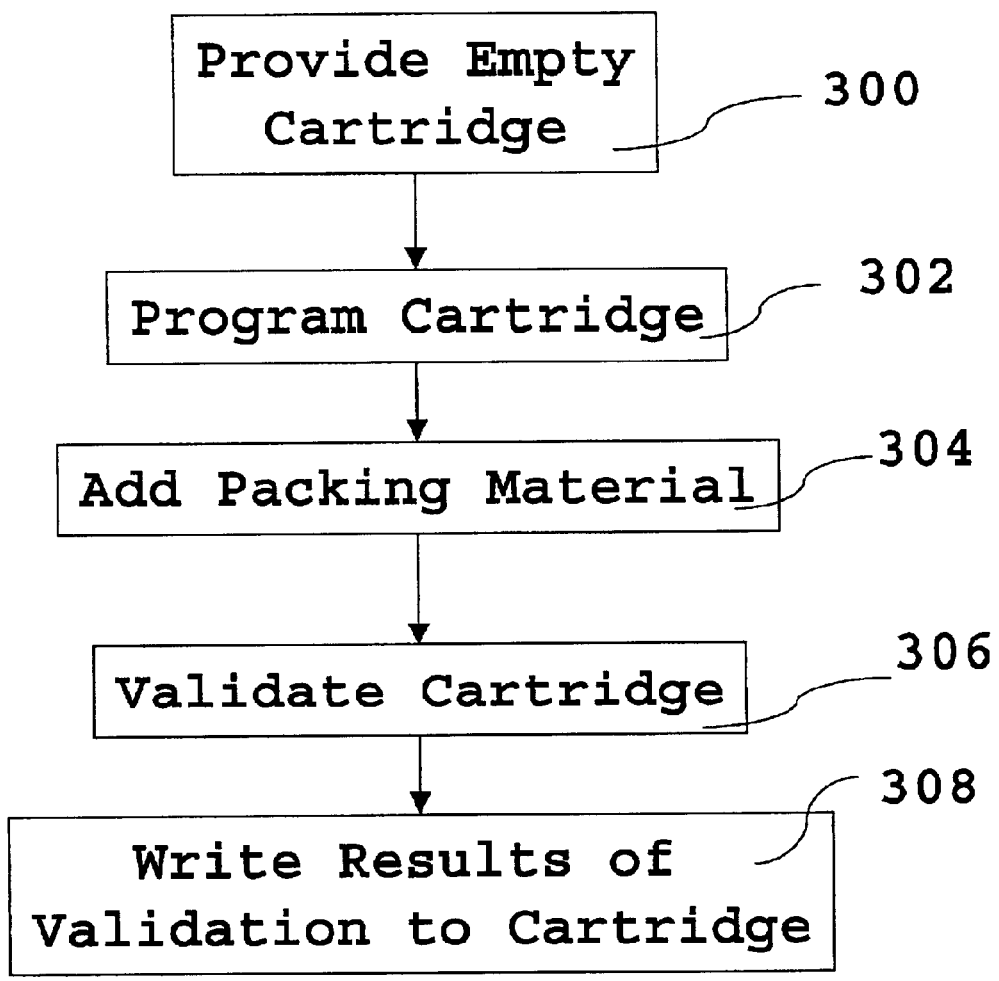
FIG. 8 is a flow diagram of the method of producing a fluid separation conduit cartridge, in accordance with preferred embodiments.

In accordance with certain preferred embodiments, a method for the construction of a fluid separation conduit cartridge comprising a memory unit is shown in FIG. 8. An assembled conduit cartridge 300 capable of performing chromatography, for example, is provided, which may comprise a potted conduit and/or a memory unit as described herein before. In embodiments comprising a memory unit, the conduit cartridge is programmed 302 or personalized, at the manufacturing site, for an intended use. That is, methods, parameters, information, data and the like are programmed into the conduit cartridge prior to shipping the conduit cartridge to the end user. In embodiments comprising a potted compound but no memory unit, this step may be omitted. The type of information written into the memory unit when it is personalized for a particular user method includes but is not limited to method parameters defining a liquid chromatographic (LC) or capillary electrophoretic (CE) or other liquid-phase separation, such as micellular electrokinetic chromatography (MEKC or MECC) separation to be employed by the particular fluid separation conduit cartridge. Other information can include but is not limited to data acquisition parameters, solvent gradient control parameters, expected target molecule names, IUPAC identifiers and retention time windows, detector response factors, other operational and analytical parameters used by commercial chromatographic data stations, the date and time of cartridge personalization and any other information desirable to or requested by an end-user. Subsequently, test performance (also known as method validation) data would typically be stored to the memory unit with the time and date obtained. The memory unit is capable of storing acquired data in its memory with an indicator of cartridge usage. Examples of different types of read/writeable memory units are discussed above and other memory units are well known to those skilled in the art. It should be appreciated that information stored onto the memory unit can be encrypted, as discussed in the commonly assigned patent applications which have been incorporated by reference for all purposes. Additional information may be coded onto the conduit cartridge in the form of a bar code, a magnetic strip, or semiconductor chip. The device employed to read the code from the fluid separation conduit cartridge will depend on the format and medium of the code contained within the memory unit, examples of which include but are not limited to bar code readers, magnetic strip readers, a radio transponder, an inductive loop, ultrasonic, infrared, direct connection, an optical detector, electrical impulse detector or a data bus socket, all of the aforementioned methods and devices being well known to those skilled in the art.

In accordance with certain preferred embodiments, the conduit cartridge is loaded or packed 304 with a suitable packing material, e.g. a stationary phase, for the intended use of the conduit cartridge. As discussed above, the chemistry, e.g. functional groups, of the stationary phase typically depends on the intended use and the nature of the species in the fluid to be separated. One skilled in the art given the benefit of this disclosure will be able to select suitable stationary phases for separating species in fluids introduced into the conduit cartridges disclosed here. The assembled and packed fluid separation conduit cartridge can be validated 306, e.g. tested, at the manufacturing site to determine if the cartridge complies with known specifications pertinent to a particular chromatographic method. For example, known analytes specific for a particular chemistry can be subjected to chromatographic separation using the newly formed fluid separation conduit cartridge and suitable fluid mobile phases. Resolution, along with other chromatographic parameters, can be determined based upon the performance of the cartridge with a given set of known analytes. This process is a similar operation to that performed when validating a chromatographic method. The information obtained from this testing can then be stored in the memory unit. This test information can subsequently be used as a benchmark for determining the performance status of the cartridge once the apparatus has left the manufacturing facility and is in the hands of an end user. If the cartridge meets approval, then the apparatus as a whole can be certified in digital format stored in the memory unit by the manufacturer.

In accordance with certain preferred embodiments, after validating the cartridge, the result of the validation process can be written 308 to the cartridge. Additionally, the specific chemistry of the packing material and any separation methods can be written into the memory unit of the conduit cartridge. For example, if the packing material comprises cationic functional groups, then a separation method for anion exchange can be written to the memory unit.

Figure 6A:
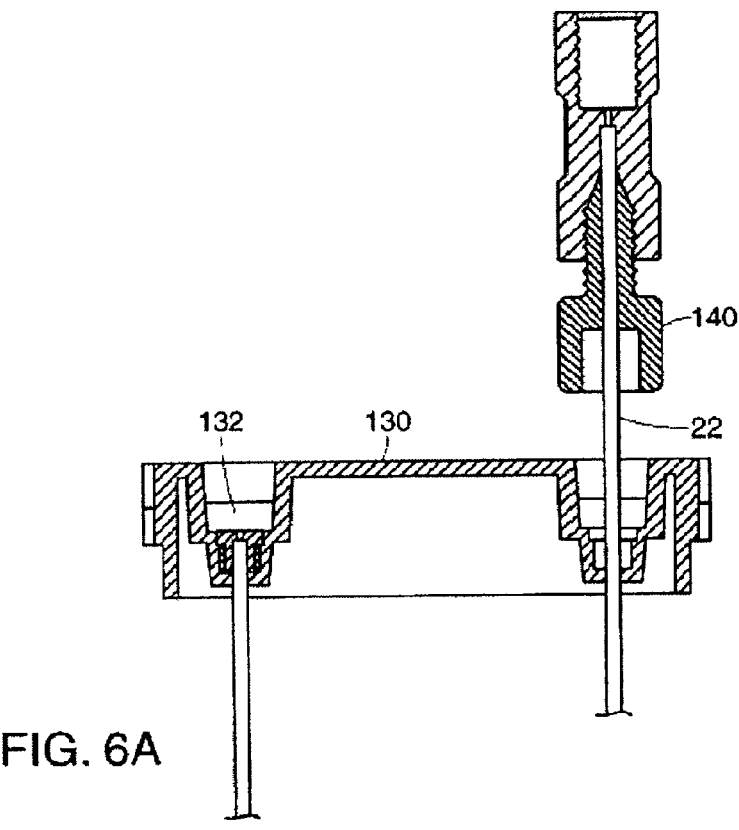
FIGS. 6a and 6b are schematic section views, partially broken away, showing the fluid separation conduit of a cartridge comprising ferrule sub-assemblies in accordance with the FIG. 4, being charged with fluid separation media, in accordance with preferred embodiments.
Figure 6B:
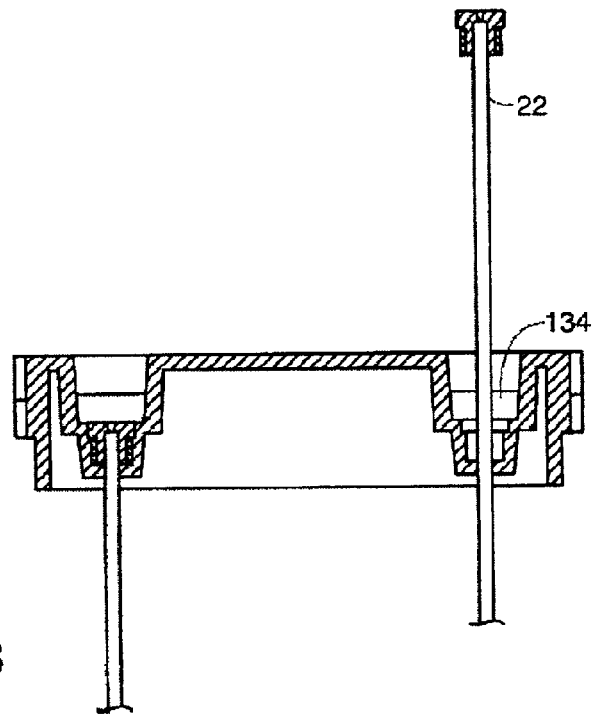

In accordance with certain preferred embodiments, a method for construction of a fluid separation conduit cartridge comprising a fluid separation conduit that is potted is disclosed. The method comprises providing an assembled conduit cartridge and disposing at least one potting compound in the housing of the conduit cartridge. The potting compound may be disposed using numerous methods known to those skilled in the art including but not limited to injecting the compound using tubing, a syringe, and the like, pouring the compound into the housing using a vessel containing the potting compound, etc. In certain embodiments, the potting compound is disposed in the housing unit prior to insertion of the fluid separation conduit. After the potting compound is disposed around the fluid separation conduit, packing material, e.g. a stationary phase, is introduced into the fluid separation conduit. The specific chemistry of the packing material typically depends on the intended use of the cartridge and the species in the fluid that are to be separated. Numerous methods for packing the stationary phase are known to those skilled in the art and include but are not limited to those mentioned above. Other methods will be readily apparent to those skilled in the art given the benefit of this disclosure. For example, FIG. 6a shows an embodiment for packing of a stationary phase into the fluid separation conduit. A device 140, preferably a needle with a syringe or tubing, is connected to the open end of a fluid separation conduit 22. The first end of the fluid separation conduit is fitted with a ferrule sub-assembly as described above, and is already seated in socket 132 of the manifold or end plate 130 of the housing unit of the conduit cartridge. After loading the packing material, an additional ferrule sub-assembly is added to the second end of the fluid separation conduit 22 (see FIG. 6b). The second end of the conduit is then pressed into socket 134 of the housing unit using manual or mechanical force or pressure, for example. Subsequent to packing the conduit, quality assurance tests may be performed on the cartridge to ensure that the cartridge will perform properly at the end user's facility. Numerous other steps may be performed after testing the cartridge, e.g. storage solvents may be introduced, the cartridge may be cleaned, etc.

Figure 9:
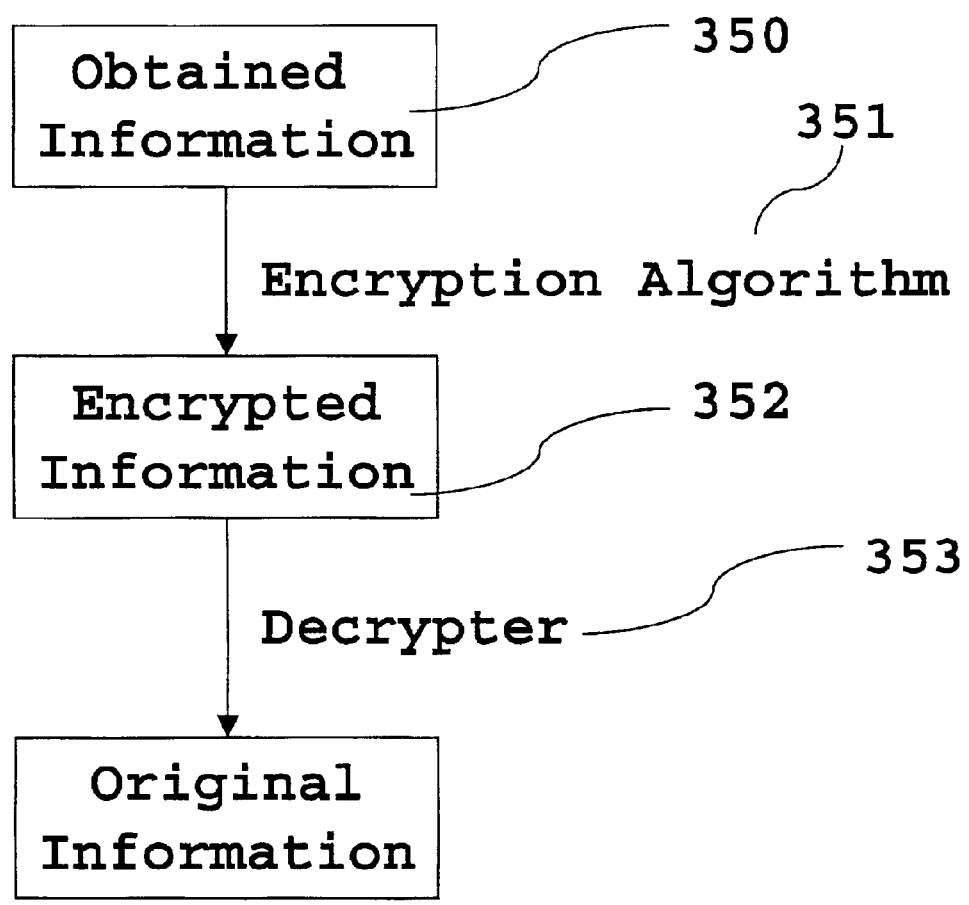
FIG. 9 shows a diagram of encrypting and decrypting information, in accordance with preferred embodiments.

In accordance with certain preferred embodiments, the conduit cartridge has the capability and is operative to compress, encrypt, transmit, receive, and decrypt information. An overview of an exemplary encryption process is shown in FIG. 9. Any information 350 that is obtained by the conduit cartridge can be encrypted using one or more encryption algorithms 351. The encryption algorithm 351 may be any algorithm known to those skilled in the art including but not limited to translation tables, word/byte rotation, Simple Key Management for Internet Protocols (SKIP), XOR bit masking, and encryption using public/private keys. Preferably the encryption algorithm used is a strong encryption algorithm, e.g. 56-bit encryption, 128-bit encryption or higher, such as DES or Blowfish though other encryption algorithms, e.g. weak encryption algorithms, may be suitable depending upon the intended use and/or location of the conduit cartridge. Once encrypted, the encrypted information 352 may not be viewed or read by anyone who does not have the proper key to decrypt the information. The decrypter or decoder 353 can convert the encrypted information back to its original form.

Figure 10:
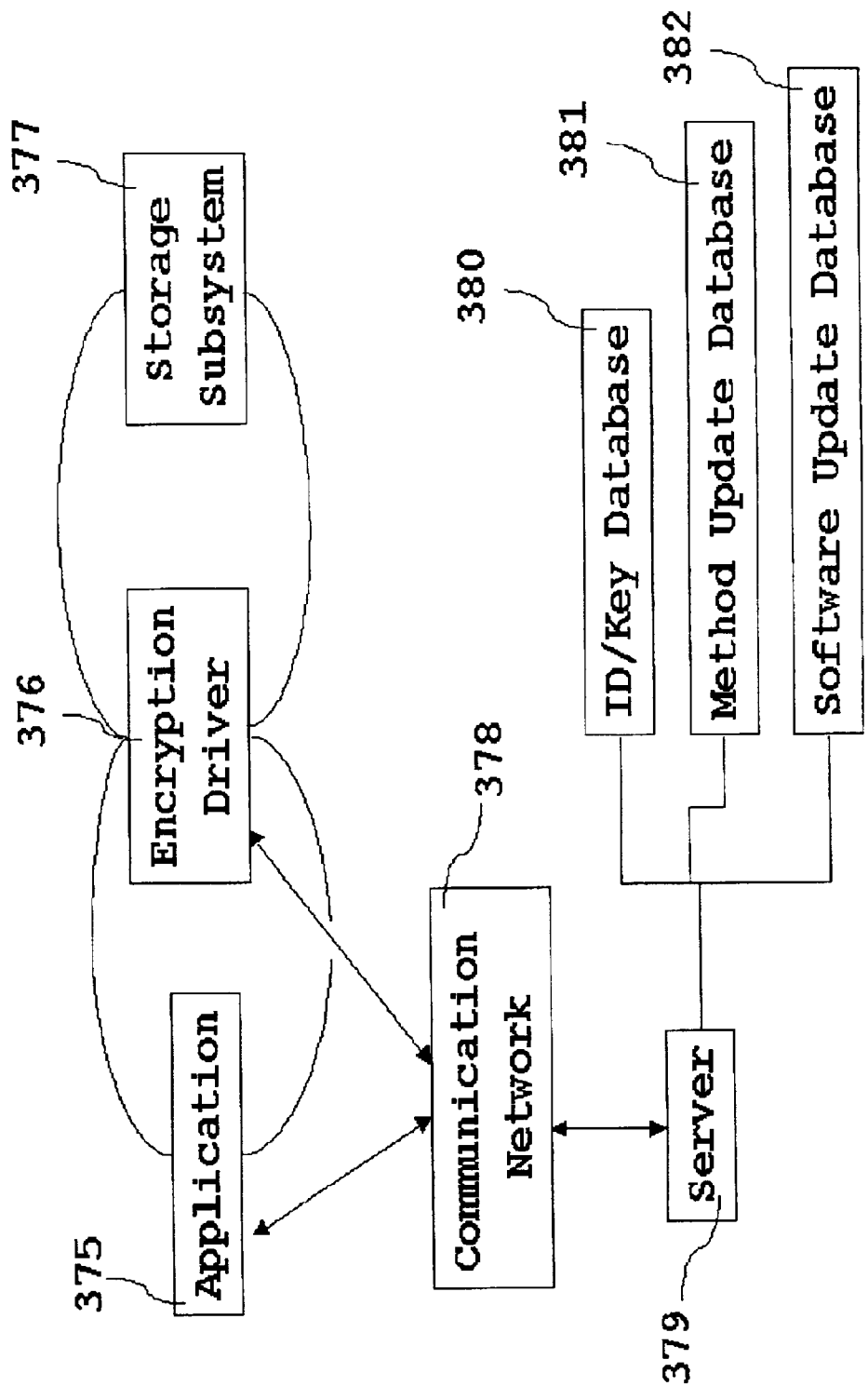
FIG. 10 shows the relationship of an encryption driver to the system comprising a conduit cartridge and an operating facility, in accordance with preferred embodiments.

In accordance with certain preferred embodiments, a two-part encryption and signing process can be used. In the first part of the encryption process, all information on the conduit cartridge is encrypted using an encryption driver. The relationship of the encryption driver to the overall encryption process is shown in FIG. 10. All information that enters or exits the conduit cartridge preferably first passes through the encryption driver 376. Applications 375, such as chromatography methods, are also encrypted by the encryption driver prior to submitting the application to the instrument. A storage subsystem 377 exists for storing encrypted information, such as methods used by the conduit cartridge or data obtained by the conduit cartridge. A communications network 378 may be used for sending information from the conduit cartridge to a server 379. The communications network 378 is also used to send information from the server 379 to the conduit cartridge. The communications network may be external, such as the Internet, or may be internal, such as direct communication between a conduit cartridge and an instrument. Preferably, all information that is sent to the conduit cartridge, either by an instrument or by a remote operating facility, first passes through the encryption driver. This information may include keys for encoding and decoding the information from the ID/Key Database 380, methods to update the conduit cartridge from the Method Update Database 381, software updates from the Software Update Database 382, or any other information that an operator desires. Preferably any and all information that is sent from the conduit cartridge to an instrument or to a server first passes through the encryption driver.

Figure 11:
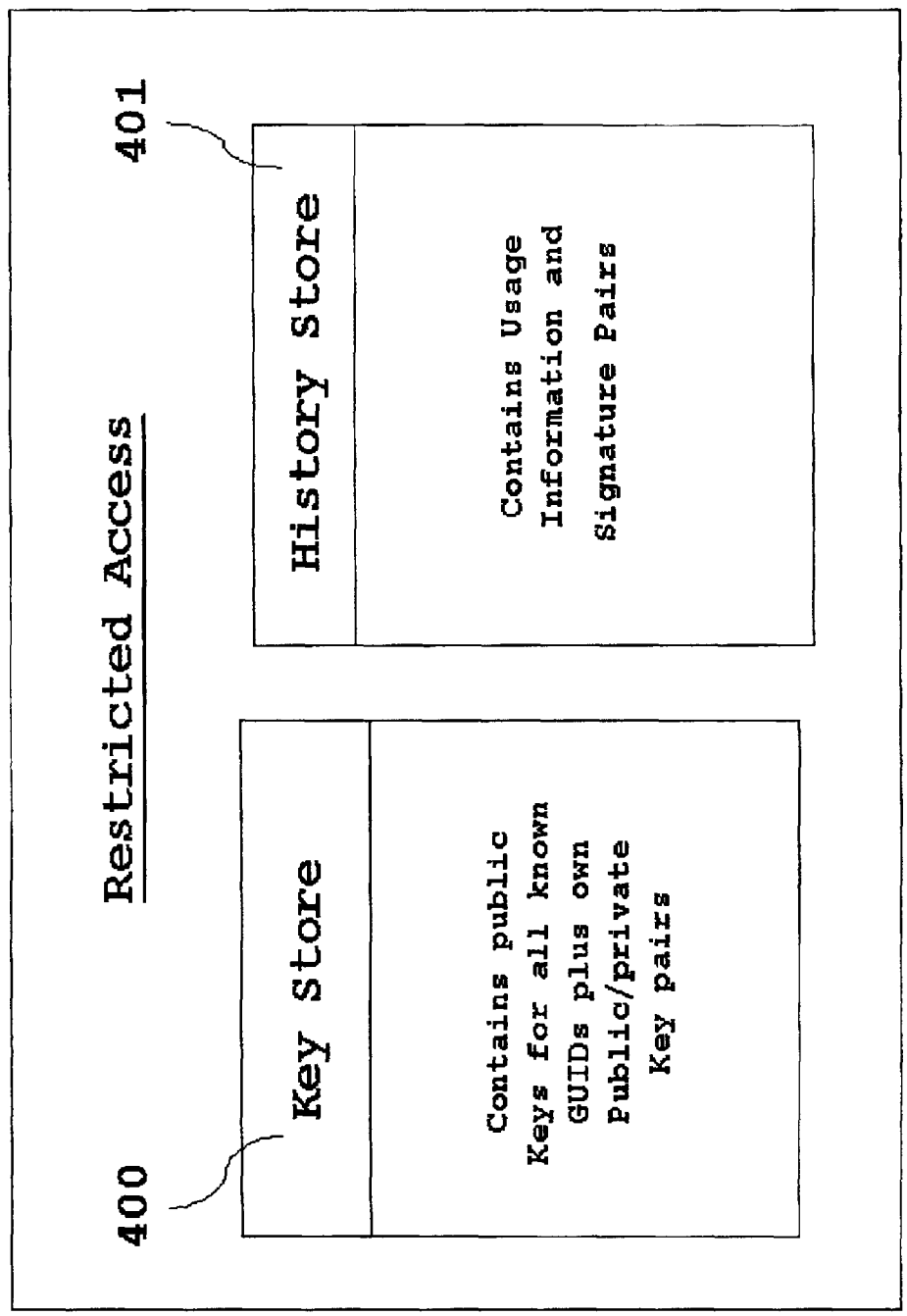
FIG. 11 shows restricted access to information on the conduit cartridge, in accordance with preferred embodiments.
Figure 12:
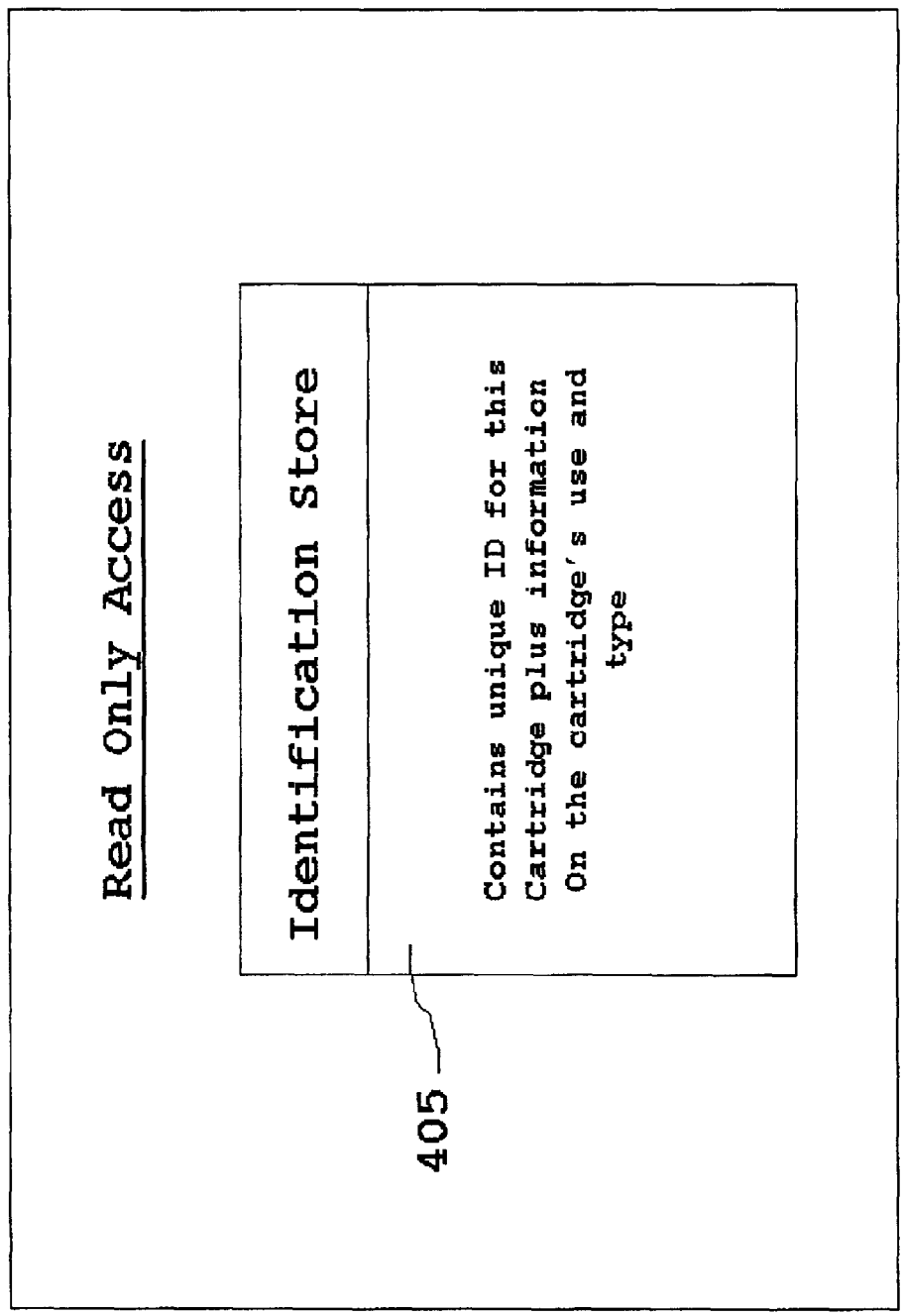
FIG. 12 shows read only access to the information on the conduit cartridge, in accordance with preferred embodiments.
Figure 13:
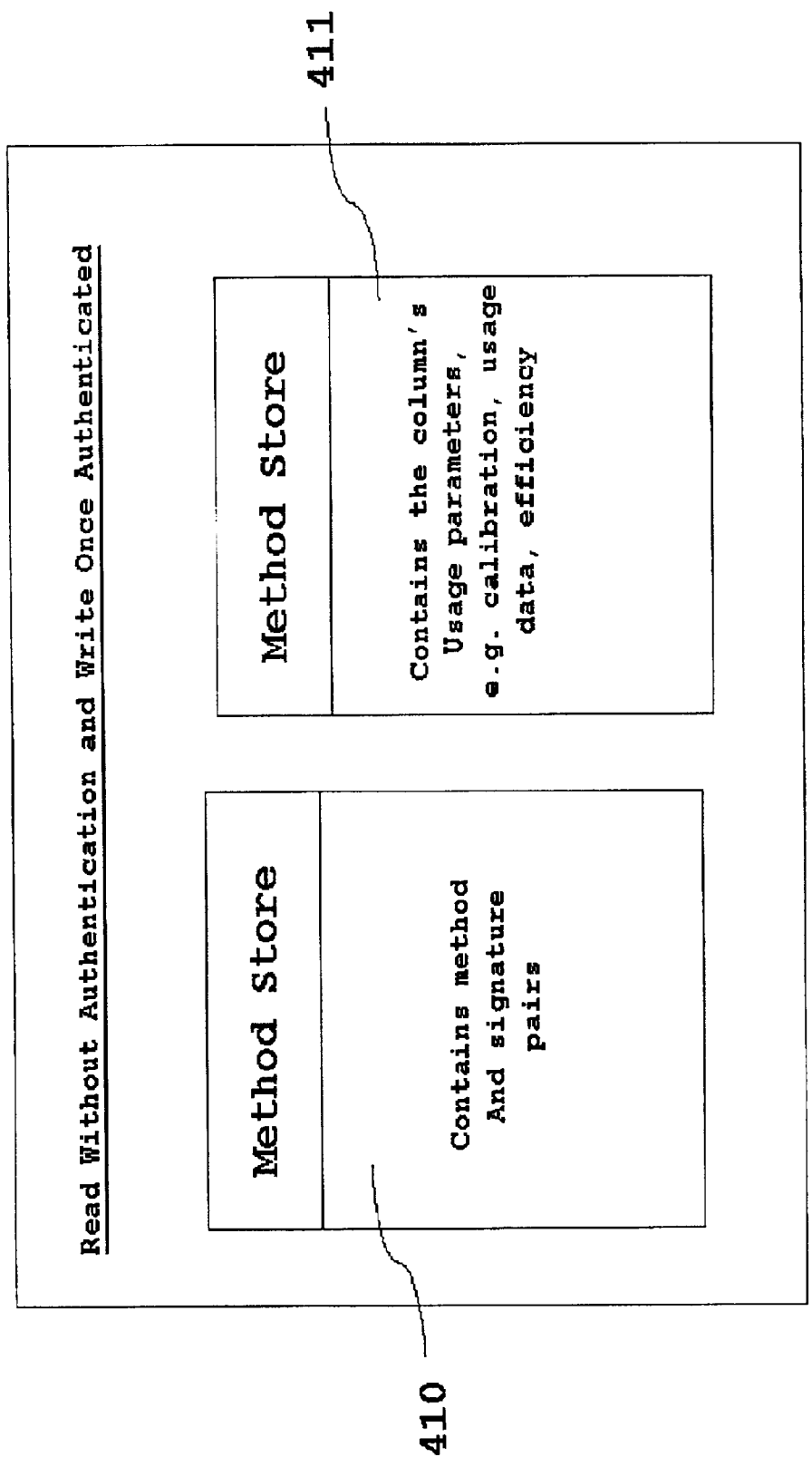
FIG. 13 shows read without authentication and write once authenticated access to the information on the conduit cartridge, in accordance with preferred embodiments.

In accordance with certain preferred embodiments, the encryption driver contains keys in an encrypted form. In preferred embodiments, the encryption driver comprises an Authentication Engine, an Encryption Engine, a Signature and Verification Engine, and a Card Filing System. The Authentication Engine provides initial access to the information on the conduit cartridge. Multiple levels of access may exist including but not limited to read-only, write only, read and write once, read and write once authorized, read and write, and restricted access. Preferably, the levels of access that exist are restricted access, read-only access, and read without authentication and write once authenticated access. Various stores are available on the conduit cartridge that have different levels of access. Preferably these stores are located in a memory unit or other electronic storage device. The level of access typically depends on the nature of the information present in the store. For example, information that is more sensitive and that should be viewed only by an authorized party having the correct decryption keys has the most restricted access. Referring to FIG. 11, to access the key store 400 and the history store 401, full authentication must be granted. The key store 400 comprises public keys for all known GUIDs and it also may comprise public/private key pairs. The history store 401 comprises usage and signature information. Since this information should be kept protected and accessed only by a system administrator, for example, it has the most restrictive access. For restricted access, the authentication system must grant both read and write access to the key store 400 and the history store 401. For read-only access, the authentication system must grant read access but not write access. Read-only access may be granted where a user wishes to view the Identification Store 405 (see FIG. 12). The Identification Store 405 contains unique identification information for the cartridge and information on the cartridge's use and characteristics. Granting of read-only access does not permit a user to alter any information on the conduit cartridge or to write any information to the conduit cartridge. For read without authentication and write once authenticated access, a store can be read without authentication, but writing to the conduit cartridge requires authentication. For example, referring to FIG. 13, to read information in the method store 410 or the parameter store 411, authentication is not required. However, to alter the information in the method store 410 or parameter store 411, authentication is required. A summary of the access rights is shown in Table I and Table II.

TABLE I

Access when Authentication is Not Performed

| | Read Information? | Write Information? |
| --- | --- | --- |
| Restricted Access | No | No |
| Read Only Access | Yes | No |
| Write Once Authenticated Access | Yes | No |

TABLE II

Access when Authentication is Performed

| | Read Information? | Write Information? |
| --- | --- | --- |
| Restricted Access | Yes | Yes |
| Read Only Access | Yes | No |
| Write Once Authenticated Access | Yes | Yes |

In accordance with certain preferred embodiments, the Encryption Engine preferably is an encryption algorithm or an encryption device that is operative, or has the capability, to encrypt and/or decrypt information. The encryption algorithm may be any algorithm known to those skilled in that art including translation tables, word/byte rotation, Simple Key Management for Internet Protocols (SKIP), XOR bit masking, and encryption using public/private keys. Preferably, the Encryption Engine uses a strong encryption method such as DES or Blowfish. The keys for the encryption may also be encrypted and stored in the Encryption Engine, and the keys may be decrypted when necessary for encrypting or decrypting information.

Figure 14:
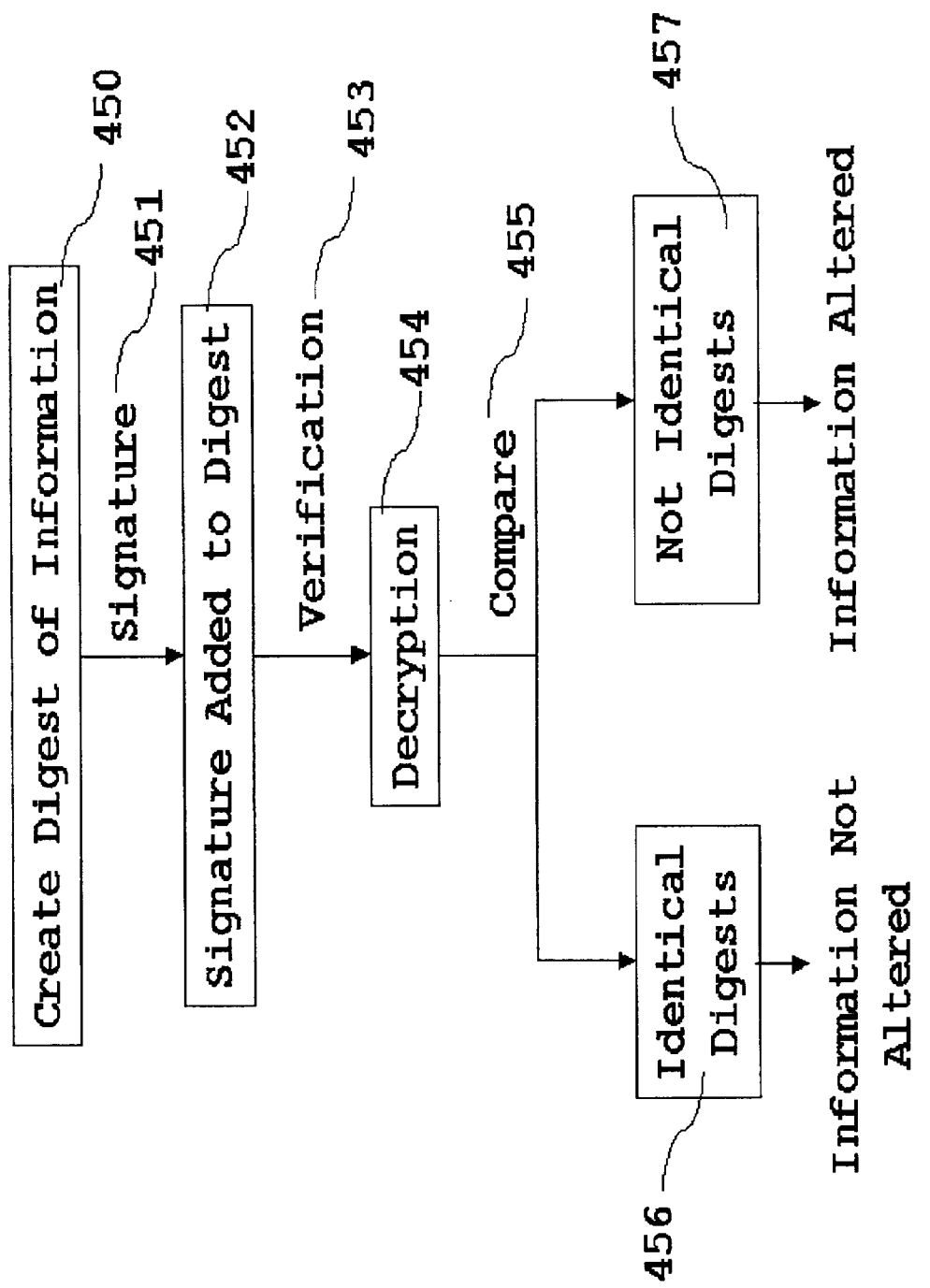
FIG. 14 shows an overview of the signature process, in accordance with preferred embodiments.

In accordance with certain preferred embodiments, a Signature and Verification Engine can be used. The Signature and Verification Engine (SAVE) is a record keeping device that signs all information to ensure that a record of events exists. The SAVE is responsible for signing and storing all information passed to the encryption driver. The SAVE is also responsible for retrieving and verifying all objects that are retrieved from the storage device. The SAVE also ensures that the key store on the cartridge is up to date and contains all relevant public keys needed to verify the signatures of information in the storage device. The signature may be used to verify that another party did not alter the information on the conduit cartridge. An overview of the signature process is shown in FIG. 14. The first step is that a digest 450 of the information is created. The digest is essentially a hash of the information that is created using an encryption algorithm. A signature 451 is then added to the digest. Preferably, the signature is added using the signer's private key. The signature that has been added to the digest 452 is then transmitted or stored along with the object to which it refers. When verification 453 of the information is required, decryption 454 of the information occurs, and a digest of the information is created using the same encryption algorithm used to generate the signing hash. Preferably, the signature is decrypted using the signer's public key. The decrypted hash is compared 455 with the generated hash. If the hashes or digests are identical 456 then the object has not been altered since the signature was generated. If the hashes or digests are not identical 457 then the object has been altered since the signature was generated. This comparison provides an added security measure to verify if the information has been tampered with by an unauthorized party. Other verification measures may be used in placed of or in addition to the SAVE. One skilled in the art given the benefit of this disclosure will be able to use the verification methods disclosed here as well as other suitable verification measures and methods.

In accordance with certain preferred embodiments, the weakest link in any encryption system that uses public/private key pairs is typically the key provider, e.g. it is easy to generate a public/private key pair locally, insert the keys into the cryptographic system, and have apparently verified and secure communications. To provide added security, a key authority can be used in the verification process of the SAVE. The key authority provides a verification that the key pair was issued to the party whom now appears to be using it. Trust for the transaction is therefore placed in the hands of the key authority. If no third party verification is in place, the system is still secure and traceable histories can still be generated. However, the user puts his trust in his ability to verify that all keys in the system are valid. Therefore, users in critical systems and environments can validate keys against a central key store. The SAVE can make a request to a central server to validate the public key for the component. Such requests can be made through the Internet, wireless transmission, and other comparable methods. This transaction need not be secure since all that is being verified is the public key. Therefore, this transaction may be carried out over a network, such as the Internet, without the need for establishment of secure or private connections.

Figure 15:
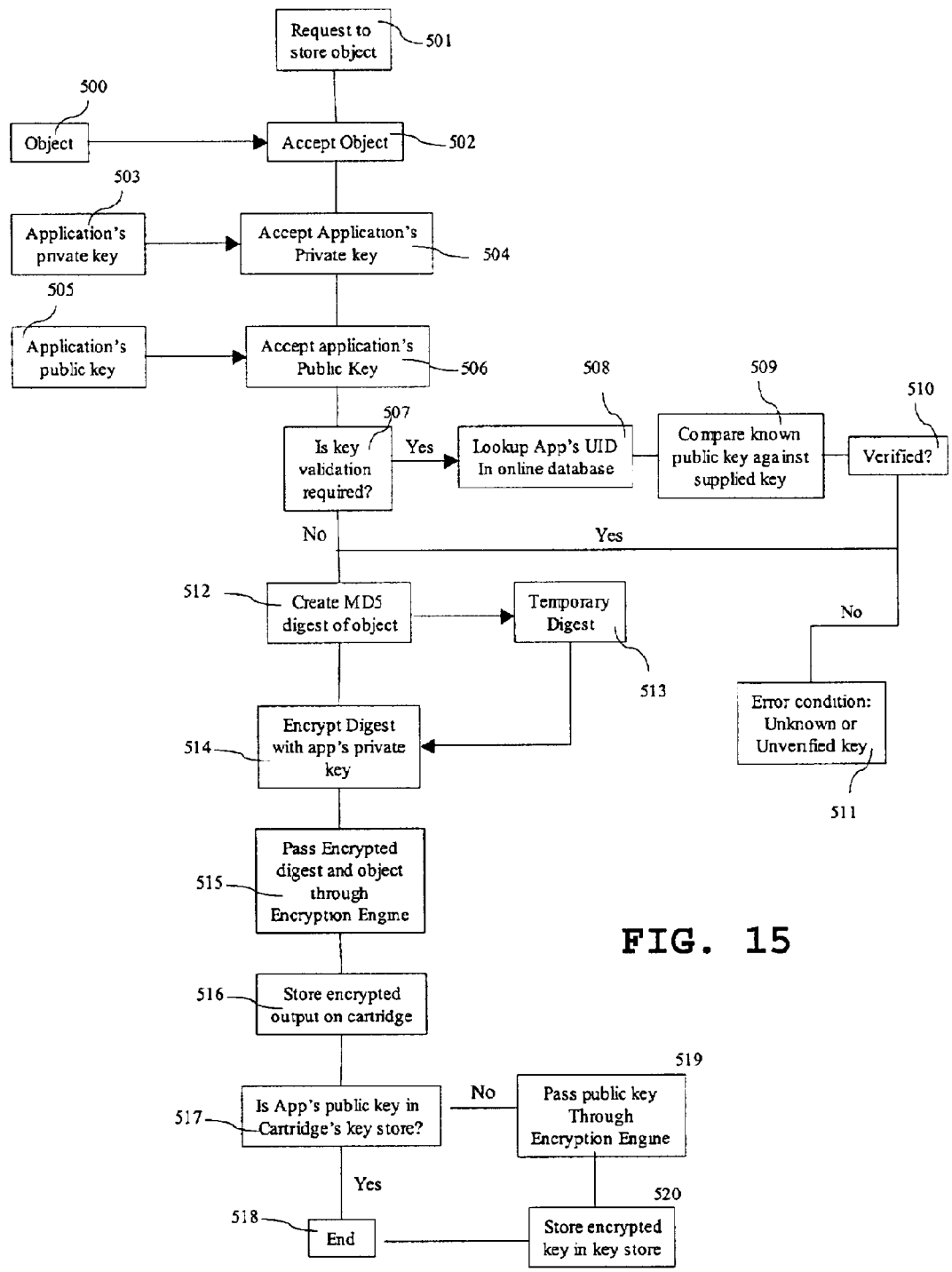
FIG. 15 shows the process of storing an object using the Signature and Verification Engine, in accordance with preferred embodiments.

In accordance with certain preferred embodiments, a process for storing an object using the SAVE is shown in FIG. 15. A request to store an object 501 is submitted to the encryption driver. The object 500 may be any information such as, for example, information in the memory unit of the conduit cartridge. Once the object is accepted 502, a private key 503 must then be accepted. After the private key is accepted 504, a public key 505 must be accepted. Once the public key is accepted 506, the system checks for key validation 507. If key validation is required the unique identifier (UID) 508 is looked up in the database. The known public key and the supplied key are compared 509. If the keys do not match, then an error is returned 511 indicating that an unknown or unverified key is in use. If the keys are verified, or if no validation is required or requested, then an digest, e.g. an MD5 digest 512, of the information is created. MD5 is a strong encryption algorithm. One skilled in the art given the benefit of this disclosure will recognize that other encryption algorithms may be used in place of the MD5 algorithm. A temporary digest 513 is then created. The temporary digest 513 is then encrypted using a private key 514. The encrypted digest and the encrypted object are passed through an encryption engine 515. The encrypted digest and the encrypted object may be stored on the conduit cartridge 516 or may be transmitted to an analytical system or a remote operating facility. If the public key corresponding to the private key used for encrypting the digest and object is present 517 on the conduit cartridge, then the process ends 518. If the public key corresponding to the private key used for encrypting the digest and object is not present 517 on the conduit cartridge, the public key may be passed through the encryption engine 519 and the encrypted key may be stored on the conduit cartridge in the key store 520.

Figure 16:
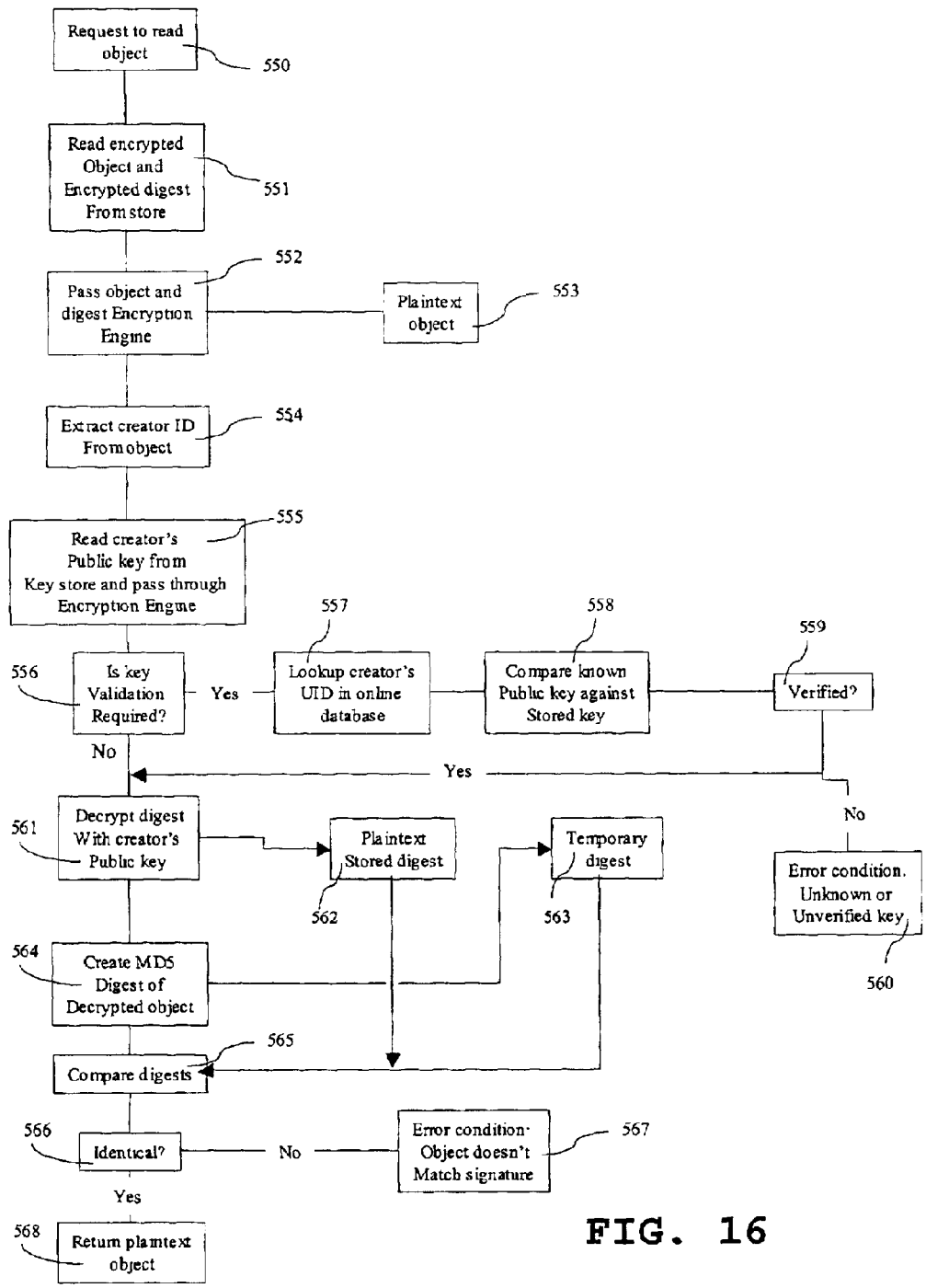
FIG. 16 shows the process of reading an object using the Signature and Verification Engine, in accordance with preferred embodiments.

In accordance with certain preferred embodiments, a process for reading an object using the SAVE is shown in FIG. 16. A request to read an object 550 is submitted to the encryption driver. The encrypted object and encrypted digest are read from the store 551. The encrypted object and encrypted digest are passed through the encryption engine 552 to create a plain text object 553 and to extract the creator ID from the object 554. The creator's public key is read from the key store and passed through the encryption engine 555. If key validation 556 is required then the creator's unique ID is looked up in the online database 557. The known public key is compared against the stored key 558. If the keys do not match, then an error is returned 560 indicating that an unknown or unverified key is in use. If the keys match, or if key validation is not required or requested, then the digest is decrypted using the public key 561 creating a plaintext stored digest 562. A MD5 digest, for example, of the decrypted object 564 is created and stored as a temporary digest 563. The temporary digest 563 and the plaintext stored digest 562 are then compared 565. If the digests do not match an error condition is returned 567 indicating that the object does not match the signature. If the digests do match then the plaintext object is returned 568 for reading. One skilled in the art given the benefit of this disclosure will recognize that other types of encryption algorithms may be used and that other methods for verifying information that are known to those skilled in the art may be used. Depending on the level of security required, one or more steps of the encryption process disclosed above may be altered and/or omitted.

Figure 17:
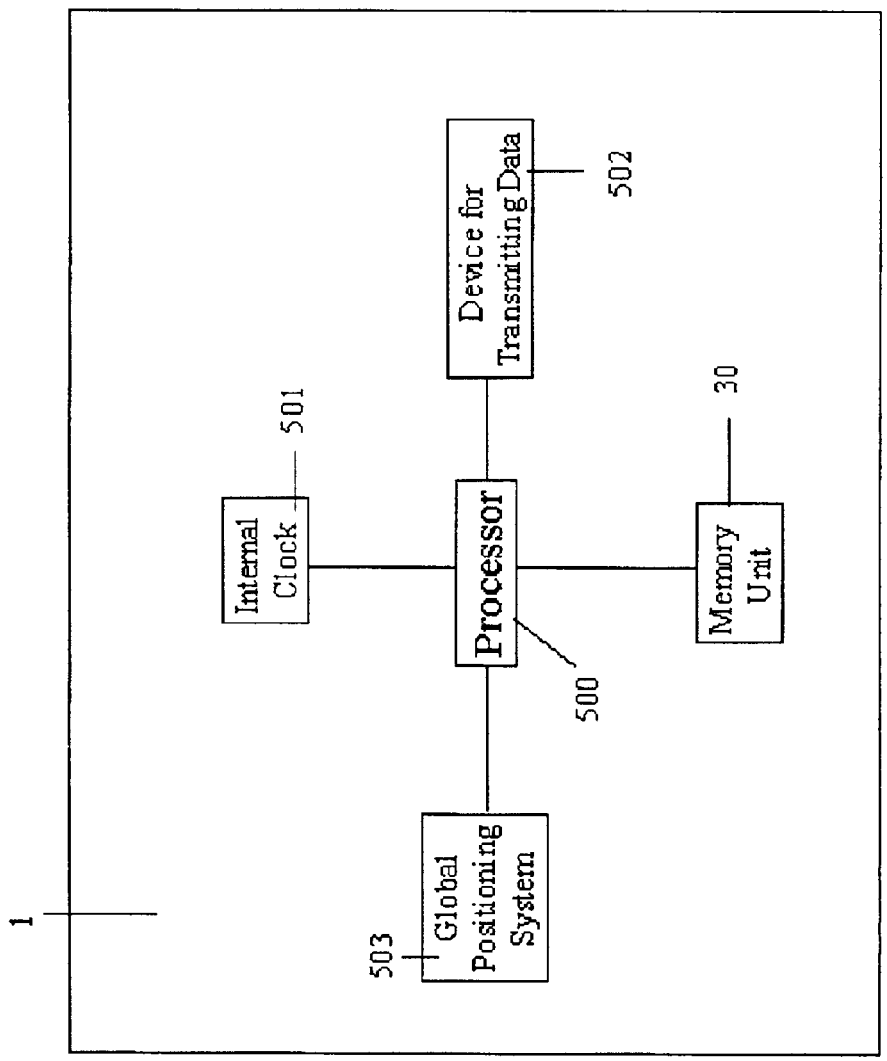
FIG. 17 shows a block diagram of several of many possible components contained within the conduit cartridge and used for encrypting, transmitting, receiving, and decrypting information, in accordance with preferred embodiments.

In accordance with certain preferred embodiments, the conduit cartridge has the capability of transmitting encrypted information to an analytical system, e.g. an instrument, or to a remote operating facility. This feature allows for automated remote field sampling and for monitoring of remote sampling processes from the operating facility. The conduit cartridge may send encrypted information by e-mail, fax, the Internet, wireless devices, satellite transmission, RF transmission, a wire connecting the conduit cartridge to the operating facility, or similar transmitting devices. For example, referring to FIG. 17, the housing unit 1 of the conduit cartridge comprises a processor 600 in communication with at least one memory unit 30. The memory unit may be any memory unit including those described here. The processor may also be in communication with an internal clock 601, a global positioning system (GPS) 603, and a transmitting and receiving device 502. Suitable transmitting and receiving devices include the devices discussed above, e.g. a modem, a fax, a wireless device, such as a cellular phone, a RF transmitter, and a satellite transmitter. Other suitable transmitting and receiving devices will be readily apparent to those skilled in the art given the benefit of this disclosure. The memory unit may contain one or more stores, tables, parameters, programs, or algorithms for compression and encryption of the information. These stores, tables, parameters, programs, or algorithms may be used to compress and encrypt the information or may be used for other purposes, e.g. a chromatography method. The processor can subsequently send the information to the transmitter for transmission to its destination. The GPS would allow for monitoring of the remote testing device by providing the absolute latitude and longitude or other geophysical coordinates (e.g. plant grid system). The GPS would also provide a tracking mechanism in the event the device is stolen. The GPS may be any GPS known to those skilled in the art, such as, for example, the GPS described in U.S. Pat. No. 06,104,340, the entire disclosure of which is incorporated herein by reference for all purposes.

Figure 18:
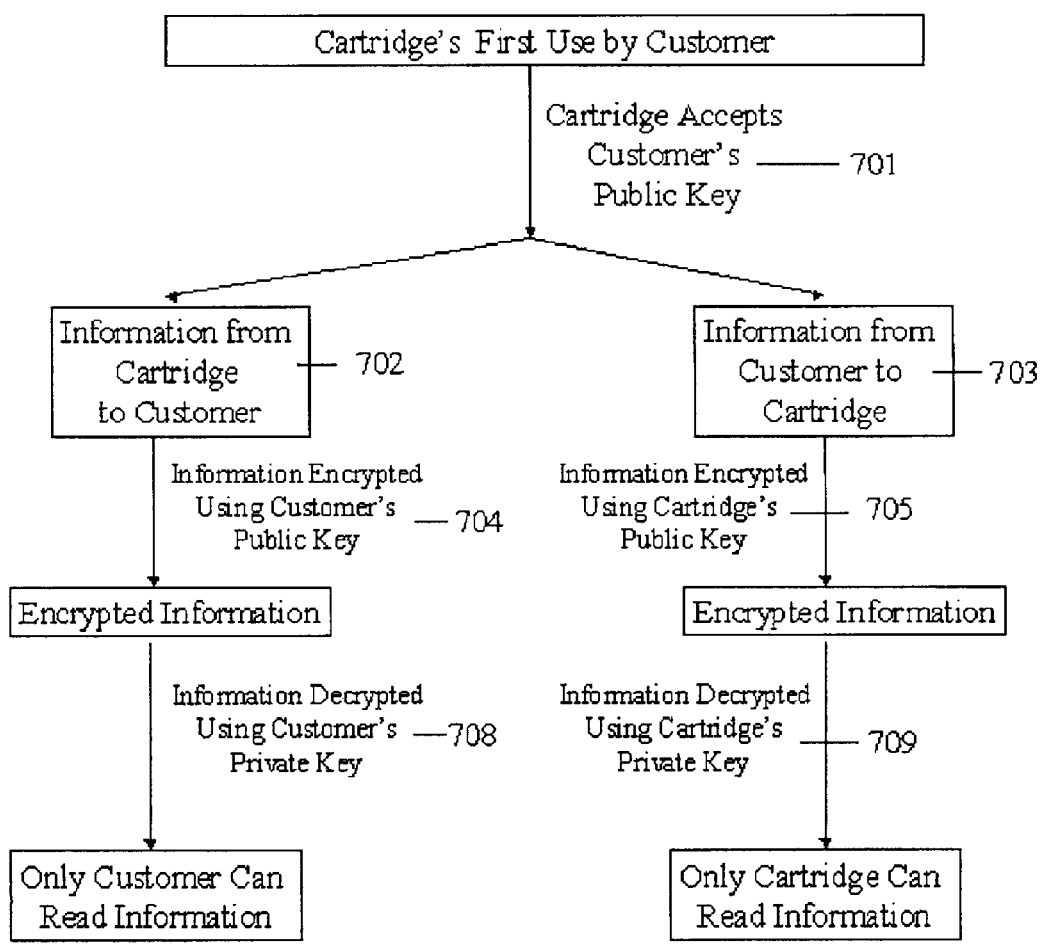
FIG. 18 is an example of a process of encryption/decryption between a customer and a conduit cartridge, in accordance with preferred embodiments.

In accordance with certain preferred embodiments, information that is sent from a conduit cartridge to a customer at a remote operating facility can be encrypted. The encrypted information that is sent from the conduit cartridge to the customer may be used for validating or posting methods, for validating or posting information, or for any other purpose deemed necessary by the customer. An example of encrypted information being sent from a conduit cartridge to a customer is shown in FIG. 18. Upon receipt by the customer, the cartridge accepts the customer's public key 701. Thereafter, exchange of information between the customer and the cartridge are encrypted and decoded using alternative public/private keys. Any information obtained by the cartridge is encrypted prior to sending to the customer 702. This information is encrypted using the customer's public key 704 and decrypted by the customer using the customer's private key 708. Therefore, only a party who possesses the customer's private key has the capability of reading the information. Any known encryption method may be used to encrypt the information that is sent from the cartridge to the customer. Preferably, a strong encryption algorithm such as DES or Blowfish is used. The information may also be encrypted using the encryption driver discussed here. Though described above as using public/private key pairs, any suitable encryption and decryption processes may be used to send information from a cartridge to a customer at a remote operating facility. One skilled in the art given the benefit of this disclosure will be able to select suitable encryption and decryption processes for sending information from a cartridge to a customer at a remote operating facility.

In accordance with certain preferred embodiments, information that is sent from a conduit cartridge to an analytical system, e.g. an instrument, in communication with the conduit cartridge can be encrypted. The encrypted information that is sent from the conduit cartridge to the instrument may be used for validating or posting methods, for validating or posting information, or for any other purpose deemed necessary by the customer. For example, referring to FIG. 19, upon plugging the conduit cartridge into the instrument, the cartridge accepts the instrument's public key 751. Information sent from the conduit cartridge to the instrument 752 is encrypted using the instrument's public key 754 and decoded by the instrument using the instrument's private key 758. Only the instrument possessing the correct private key can read the information. Any known encryption method may be used to encrypt the information that is sent from the conduit cartridge to the instrument. Preferably, a strong encryption algorithm such as DES or Blowfish is used. The information may also be encrypted using the encryption driver discussed here. Though described above as using public/private key pairs, any suitable encryption and decryption processes may be used to send information from a cartridge to an analytical system in communication with the cartridge. One skilled in the art given the benefit of this disclosure will be able to select suitable encryption and decryption processes for sending information from a cartridge to an analytical system in communication with the cartridge.

In accordance with certain preferred embodiments, to ensure that information sent from the conduit cartridge to the customer or information sent from the conduit cartridge to the instrument is received, a confirmation receipt may be sent back to the conduit cartridge. For example, if a conduit cartridge e-mails an instrument to change the method of the instrument, the conduit cartridge would have no measure or indication if the instrument received the information and subsequently implemented the new method. Those skilled in the art would recognize that many e-mail systems have the ability to send a receipt, e.g confirmation, to the message source that the message has been received or read, and the e-mail system can time stamp messages when they are sent and received. This process prevents the ineffective transmission of information from the conduit cartridge to the instrument or from the conduit cartridge to the customer. It also prevents the instrument from performing methods that are no longer desired.

Figure 19:
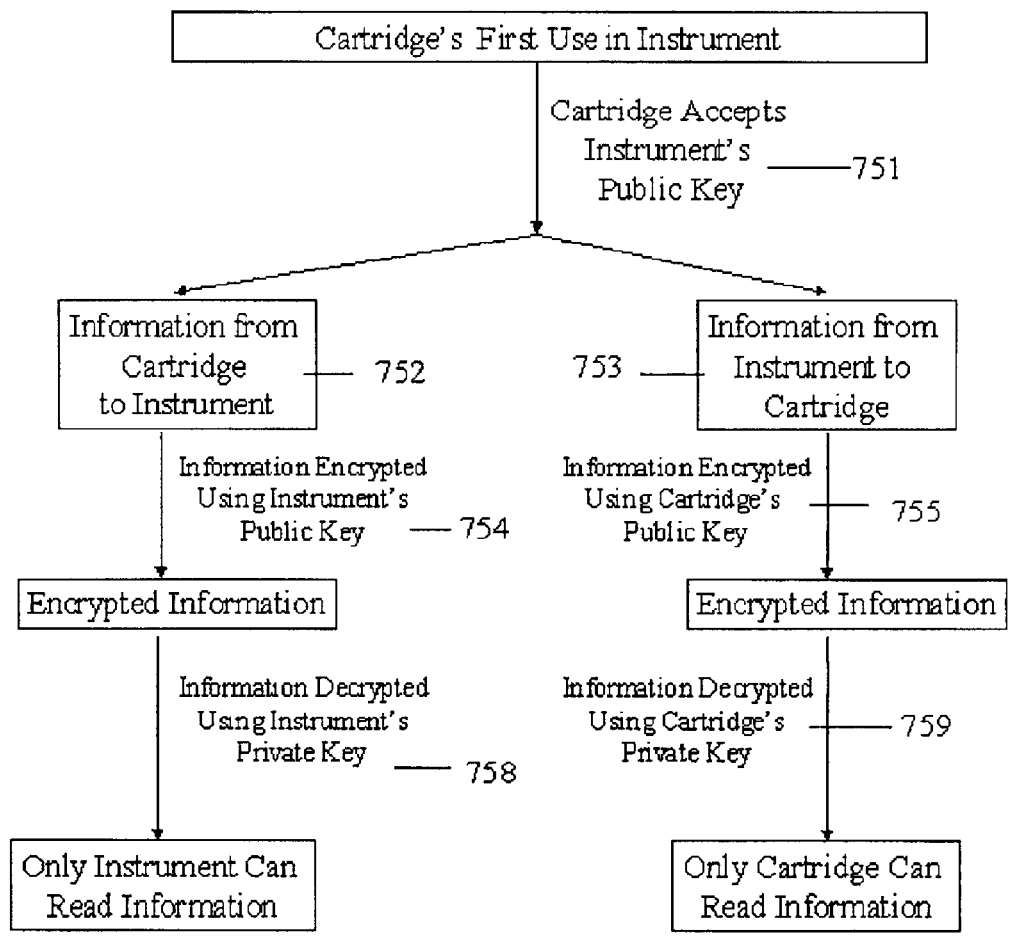
FIG. 19 is an example of a process of encryption/decryption between a conduit cartridge and an instrument, in accordance with preferred embodiments.

In accordance with certain preferred embodiments, the conduit cartridge has the capability of receiving encrypted information sent from an instrument or a remote operating facility. This feature allows for automated remote field sampling and for monitoring of the remote sampling process from the monitoring facility. The cartridge may receive encrypted information by e-mail, fax, the Internet, a wireless device, a satellite receiver, a wire connecting the conduit cartridge to the operating facility, or by a similar receiving devices. The encrypted information that is sent by the customer and received by the conduit cartridge may be used to alter the method of the instrument or to change other parameters contained within the conduit cartridge. For example, referring to FIG. 18, upon receipt by the customer, the conduit cartridge accepts the customer's public key 701. Thereafter, exchange of information between the customer and the cartridge are encrypted and decoded using alternative public/private keys. Any information that is sent by the customer to the conduit cartridge can be encrypted prior to sending the information to the conduit cartridge. This information is encrypted using the cartridge's public key 705, for example. After receipt by the conduit cartridge, the encrypted information is decrypted by the cartridge using the cartridge's private key 709. Therefore, only the cartridge with correct key may decode the message effectively preventing decoding of the message by a cartridge that receives the message in error. Any known encryption method may be used to encrypt the information that is sent from the customer to the cartridge. Preferably, a strong encryption algorithm such as DES or Blowfish is used. The information may also be encrypted using the encryption driver discussed here. Referring to FIG. 19, when the cartridge is first used in an instrument, the cartridge accepts the instrument's public key 751. Information sent from the instrument to the cartridge 753 is encrypted using the cartridge's public key 755. After receipt by the conduit cartridge, the encrypted information is decrypted using the cartridge's private key 759. Only the cartridge with correct key may decode the message. The instrument can e-mail secure summaries of each run back to the cartridge to allow updates of actual cartridge usage history including, but not limited to, increment run number, date and time of run, and any error conditions (i.e. cartridge overpressure, column blockage, etc). Any known encryption method may be used to encrypt messages that are sent from the instrument to the cartridge. Preferably, a strong encryption algorithm such as DES or Blowfish is used. The information may also be encrypted using the encryption driver discussed here. One skilled in the art given the benefit of this disclosure will be able to select other suitable encryption and decryption processes for sending information from an analytical system or a remote operating facility to a cartridge.

In accordance with certain preferred embodiments, to ensure that the information sent from the customer to the conduit cartridge or information sent from the instrument to the conduit cartridge is received, a confirmation receipt may be sent back to the source of the information. For example, if a customer e-mails a remote conduit cartridge to change the method of the conduit cartridge, the customer would have no measure or indication if the conduit cartridge received the message and subsequently implemented the new method. As discussed above, many e-mail systems have the ability to send a receipt to the source that the message has been received or read, and the e-mail system can time stamp messages when they are sent and received. This process prevents the ineffective transmission of information from the customer or instrument to the conduit cartridge. It also prevents the conduit cartridge or instrument from performing methods that are no longer desired.

Figure 20:
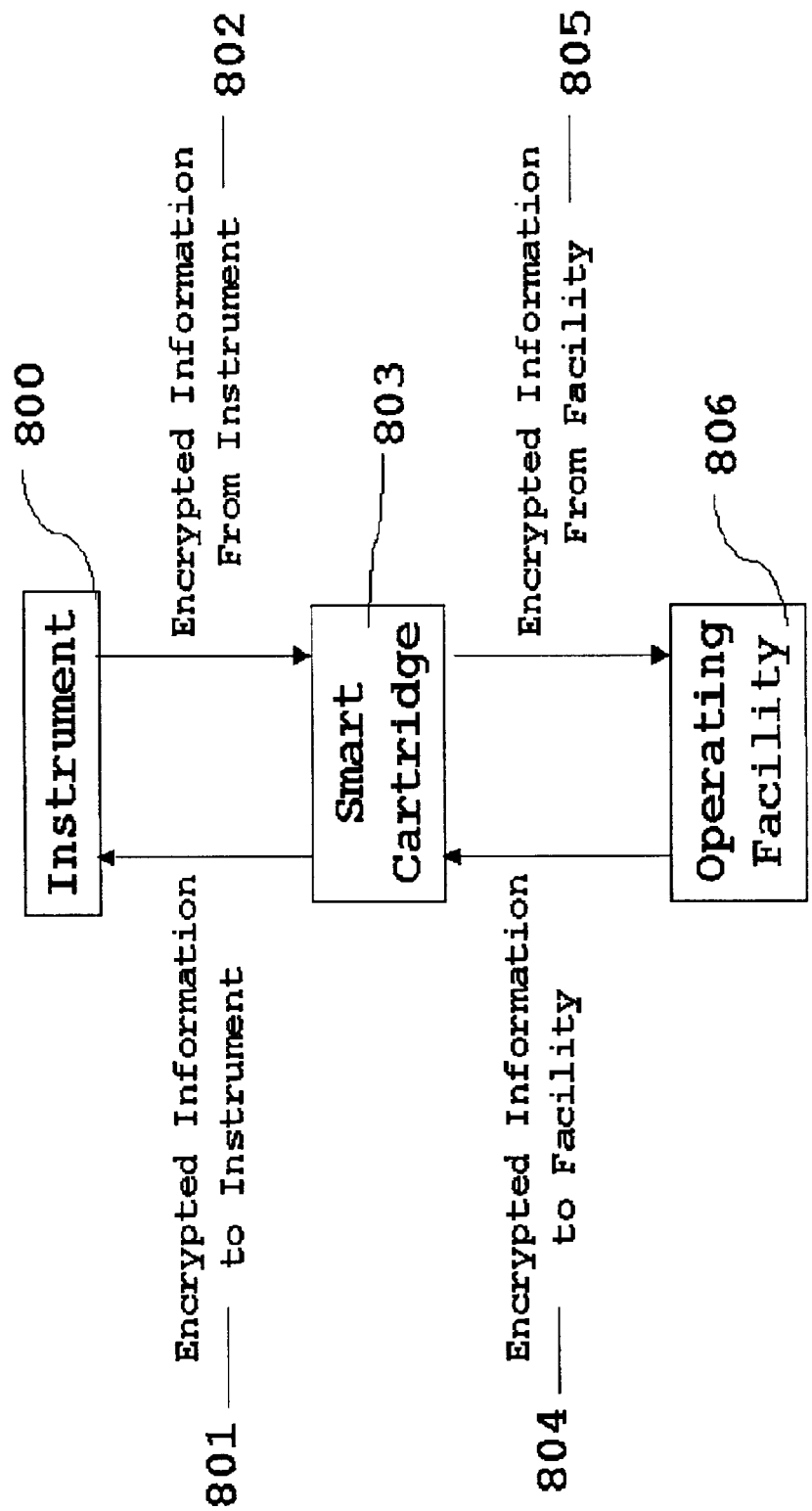
FIG. 20 is an example of encryption, decryption, reception and transmission by a conduit cartridge in communication with an instrument and an operating facility, in accordance with preferred embodiments.

In accordance with certain preferred embodiments, the conduit cartridge has the capability of receiving, decrypting, encrypting, and transmitting information simultaneously. For example, referring to FIG. 20, the conduit cartridge 803 is in communication, either by wire communication, direct communication, or by wireless communication, with an instrument 800 and with an operating facility 806. Information may be sent simultaneously to and from the conduit cartridge 803. In this example, encrypted information is sent from the conduit cartridge to the instrument 801. The information may be any information described here, such as, for example, a new method for analysis. The operating facility 806 receives encrypted information from the conduit cartridge 804. The information may include any information described here, such as data obtained from an analysis. Information can be sent from the operating facility to the cartridge 805. The information may be any information described here, such as a new method for analysis. The instrument 800 can send encrypted information to the conduit cartridge 802. This information may be any information described here, such as data obtained from an analysis. Upon receiving information, the conduit cartridge may store the information or pass the information on to the instrument 800 or operating facility 806, as the case may be. If necessary, the conduit cartridge may decrypt the information it receives from the instrument or the operating facility. Since the instrument and the operating facility may decrypt and encrypt the information using different keys, the conduit cartridge may act to decrypt and subsequently re-encrypt information. For example, if information is sent from an instrument to a conduit cartridge 802 (see FIG. 20), the information may be encrypted using the cartridge's public key (see 755 in FIG. 19). The information may then be decrypted using the cartridge's private key. Prior to transmission of the information to the operating facility, the decrypted information can be re-encrypted using the operating facility's public key. The conduit cartridge may then transmit the encrypted information to the operating facility using any transmission device disclosed here. Upon arrival at the operating facility, the information can be decrypted using the operating facility's private key. Therefore, multiple keys are required to obtain and view information that is acquired by the instrument in communication with a conduit cartridge and subsequently sent to an operating facility. This feature provides for extra security, e.g. an unauthorized user may need more than one key to view the information. One skilled in the art would recognize that the encryption driver disclosed here could also be used to encrypt and decrypt the information or other suitable encryption and decryption processes may be used.

In accordance with certain preferred embodiments, a similar process can occur when information is sent from the operating facility to the conduit cartridge. The information can first be encrypted using the cartridge's public key. The information can be transmitted by the operating facility and received by the conduit cartridge. The conduit cartridge can then decrypt the information using the cartridge's private key. If the information was intended for the instrument in communication with the conduit cartridge, the conduit cartridge would then re-encrypt the information using the instrument's public key. The encrypted information would be transmitted to the instrument. Upon arrival at the instrument, the instrument, using the instrument's private key, would decrypt the encrypted information. Therefore, multiple keys are required to obtain and view information that is sent from the operating facility, received by the conduit cartridge and subsequently sent to an instrument in communication with the conduit cartridge. These features provide added security measures to protect data and/or any other information sent to or sent by the conduit cartridge.

In accordance with certain preferred embodiments, while encryption of the information provides for secure transmission and reception of the information, it may not necessarily provide for efficient transmission and reception of the information. The information obtained by the conduit cartridge may consist of multiple parameter tables that must be sent to a remote operating facility, for example. Transmission and reception of large amounts of information, by e-mail, the Internet, or other transmission and reception devices and methods discussed here, would require a significant amount of time. It would be desirable to keep the amount of time required for transmitting and receiving the information to a minimum. Data compression can be used to decrease the amount of time required for transmission and reception of the information by decreasing the size of the information that is sent. Additionally, several compression algorithms also provide some degree of data encryption. For example, one data compression algorithm might convert a stream of symbols forming an input message into an encoded stream of symbols forming an output message. The input message may be reconstructed upon expanding the output message. An additional type of data compression technique is known as a dictionary-based compression. This technique uses codes for strings of symbols of an input message stream, thereby effectively reducing the size of the output message. A dictionary-based compression method maintains a table of recognized strings. Strings in the input stream that match the string entries that are stored in the dictionary are encoded using a code representing the corresponding dictionary entries. The compression methods discussed above, and other comparable compression methods, enable faster transmission and receipt of the information, may provide an added measure of encryption and security, and require less memory and processing power to encrypt, transmit and receive the information. One skilled in the art would recognize that any compression method may be used to compress the information on the conduit cartridge. One skilled in the art would also recognize compression may be performed prior to or after encryption of the information.

Figure 21:
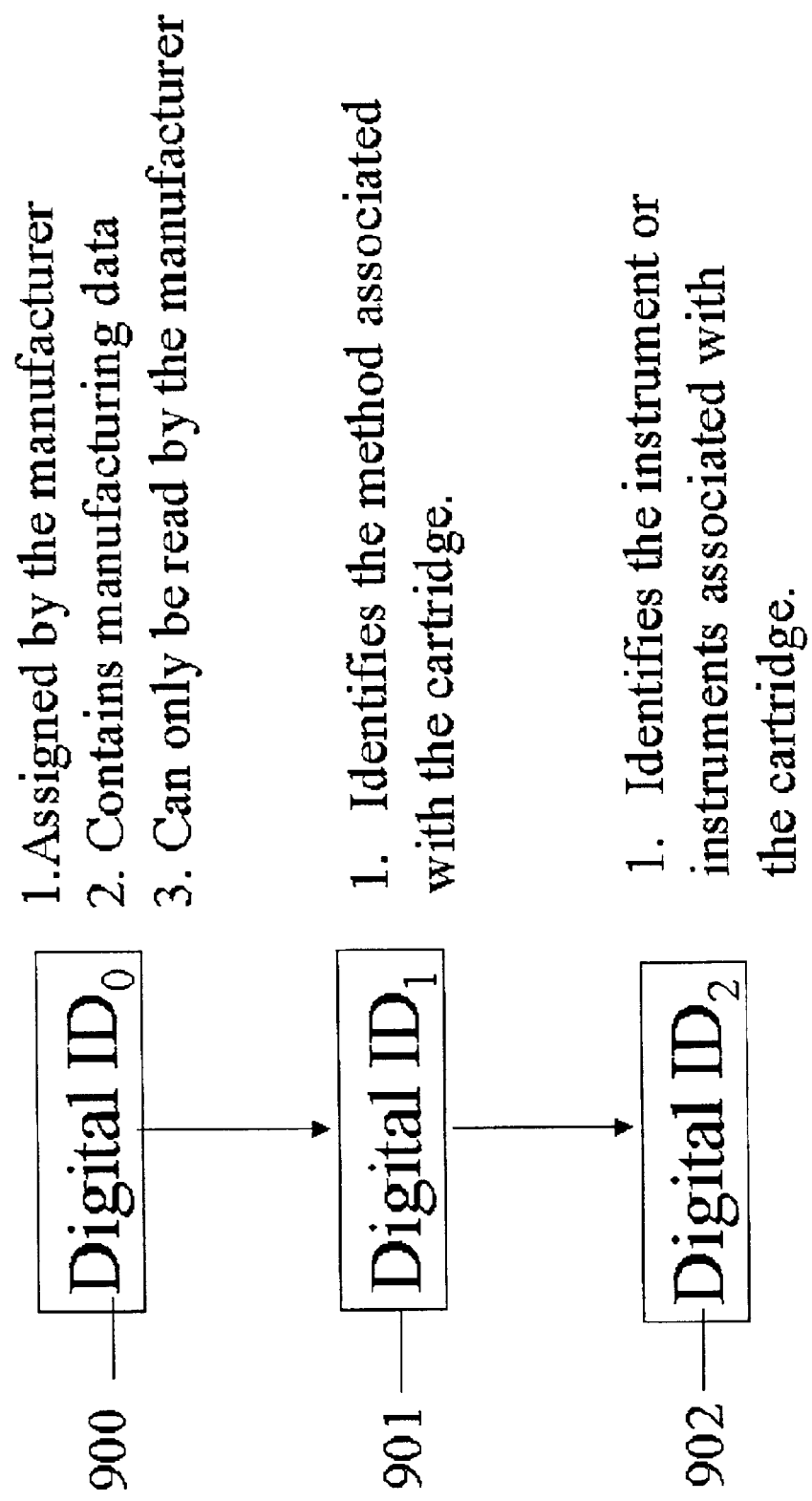
FIG. 21 is an example of the assignment of digital IDs to the conduit cartridge.

In accordance with certain preferred embodiments, the conduit cartridge may include one or more digital IDs. Referring to FIG. 21, a digital ID 900 is created for the conduit cartridge ($ID_0$). The information encrypted with $ID_0$ cannot be changed or read except by the manufacturer. $ID_0$ effectively identifies the conduit cartridge by cartridge manufacturer, design revision, lot number, manufacturing date, and any other parameters deemed appropriate by the manufacturer. A second digital ID 901 can be created, $ID_1$, that identifies the method associated with the conduit cartridge. A third digital ID 902 can be created, $ID_2$, that identifies the instrument or instruments associated with the conduit cartridge. Assignment of digital IDs to the conduit cartridge provides one or more unique identifiers, some of which cannot be altered by an end-user ($ID_0$), to the conduit cartridge. Additionally, if the conduit cartridge is removed from the instrument, a time stamp may be recorded, possibly within one of the digital IDs or as another digital ID, for example. One skilled in the art given the benefit of this disclosure will recognize that other digital Ids may be created and written to the conduit cartridges disclosed here.

Several examples of a fluid separation conduit cartridge are described below. The examples are not intended to limit the fluid separation conduit cartridges described here in any manner.

EXAMPLE 1

Figure 22:
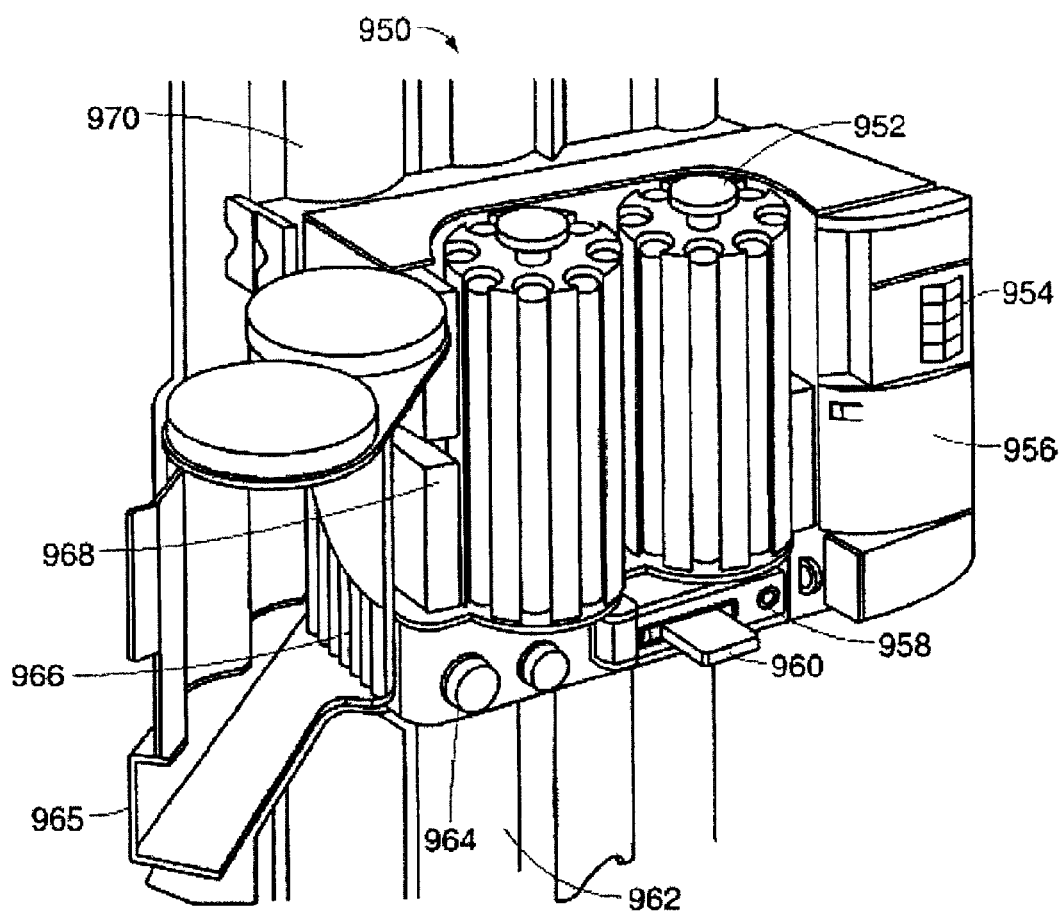
FIG. 22 is a first embodiment of an analytical system in communication with a fluid separation conduit cartridge, in accordance with preferred embodiments.

An example of a fluid separation conduit cartridge interfaced with an analytical system, e.g. a chromatography system, is shown in FIG. 22. The analytical system typically is positioned within an end-user's facility for automated analyses. That is, the analytical system may be positioned near, or in-line, e.g. within the sample flow itself, such that analysis of samples may occur automatically, e.g. using auto-samplers, auto-injectors, and the like, or to facilitate rapid analysis of samples, e.g. samples during a process by an operator at an end-user's facility. For example, the system can be configured for analysis at specified intervals, e.g. every minute, hour, day, etc., such that continuous monitoring of a process can be performed with little or no user input. That is, the system can be configured to run a chromatographic method at a specified time interval without additional input from an operator. Referring to FIG. 22, the analytical system 950 typically comprises a conduit cartridge 960 interfaced with an analytical system, e.g. a chromatography instrument. Numerous mechanisms for interfacing the conduit cartridge with the analytical system are known to those skilled in the art and exemplary interfaces are described below. The analytical system optionally comprises a treatment unit 952, such as a filter, a guard column, a solid phase extraction silo for analyte preconcentration, etc. The analytes may be pre-concentrated such that trace levels of analyte are concentrated to levels that are detectable by the analytical system. That is, the concentration of an analyte may be increased $10^1$, $10^2$, $10^3$ $10^4$, $10^5$, $10^6$, $10^7$, $10^8$, $10^9$ times or higher to levels that are easily detected using the detector of the analytical system. The treatment units are optional and may be replaced with other chromatographic devices, such as, for example, guard columns, filters, semi-permeable membranes, etc. Alternatively, the treatment units can be replaced with a fluid flow channel such that little or no operations are performed on the fluid prior to entry into the conduit cartridge.

The system also typically includes a graphical user interface 954 for programming the system, e.g. the method, and/or monitoring system performance. The graphical interface may take numerous forms such as, for example, a keypad, an LCD screen, a touch screen, e.g. a touch screen display unit, etc. In certain embodiments, the graphical user interface is omitted and the information on the conduit cartridge is used to program the system. The system optionally contains a receiver/transmitter 956 to provide for remote operation and diagnosis, e.g. operation of the analytical system over the Internet and/or transmission of data over the Internet to a remote facility. In certain embodiments, the conduit cartridge itself comprises a receiver/transmitter, and thus the receiver/transmitter of the analytical system may be omitted.

The system typically includes at least one detector 958. The type of detector used typically depends on the optical and physical properties of the species in the fluid. Preferred embodiments of the detector include at least a flow cell, e.g. a flow cell detector in communication with the cartridge. Additionally, the detectors are usually interchangeable such that the detector may be switched to a different type of detector, e.g. from a UV-Visible absorbance detector to a fluorescence detector. Suitable detectors include but are not limited to UV-Visible absorbance detectors, IR detectors, fluorescence detectors, electrochemical detectors, voltammetric detectors, coulometric detectors, potentiometric detectors, thermal detectors, ionization detectors, NMR detectors, EPR detectors, Raman detectors, refractive index detectors, ultrasonic detectors, photothermal detectors, photoacoustic detectors, evaporative light scattering detectors, mass-spectrometric detectors, and the like. The conduit cartridge 960 typically interfaces with the system through a manifold, which is discussed in detail below. In alternative embodiments, however, the conduit cartridge can interface directly with the system, e.g. can be connected directly to a fluid supply source, e.g. a pump and/or injector, without any intervening mechanical components, for example.

A closeable face plate 965 may be hingeably or removably attached to the system and can be closed over, or around, the system to protect the system from harsh environmental conditions, such as chemical solvents, UV radiation and the like. Supplying power and data to the chromatography system is a power and communication interface 966. Such interfaces typically are operative to provide a power source to the system, and can also provide communication of the system to a central computer, e.g. a computer in communication with the system for monitoring test results and/or for receiving information from the system.

To achieve high reproducibility, a fixed-loop injector 964 is typically used to introduce sample into the system. Suitable fixed-loop injectors are well known to those skilled in the art and are commercially available from numerous sources, e.g. Beckman Instruments (Fullerton, Calif.). Other injectors may be used in place of the fixed-loop injector depending on the intended use of the system. For example, auto-injectors and/or auto-samplers may be used to provide for automated sampling and analysis of fluids. Suitable auto-samplers and auto-injectors are well known to those skilled in the art and are commercially available from numerous manufacturers. Optionally, the system can be programmed such that the auto-samplers and/or auto-injectors take samples at specified intervals, e.g. every 10 seconds, every minute, hourly, daily, weekly, monthly, etc., such that testing of the fluid can be performed without any input from a user. The system also includes precise microfluidics for accurate solvent gradients and includes solvent reservoirs and/or reagent magazines 968 for providing a fluid phase for running the chromatographic methods of the conduit cartridge, e.g. solvent gradients and the like. Such precise microfluidics can be achieved using numerous methods known to those skilled in the art, such as the methods described in the commonly assigned U.S. Patent Applications incorporated herein by reference for all purposes. As discussed above, typically in fluid communication with the solvent reservoirs are one or more pumps, which are operative to generate a fluid flow.

Figure 23:
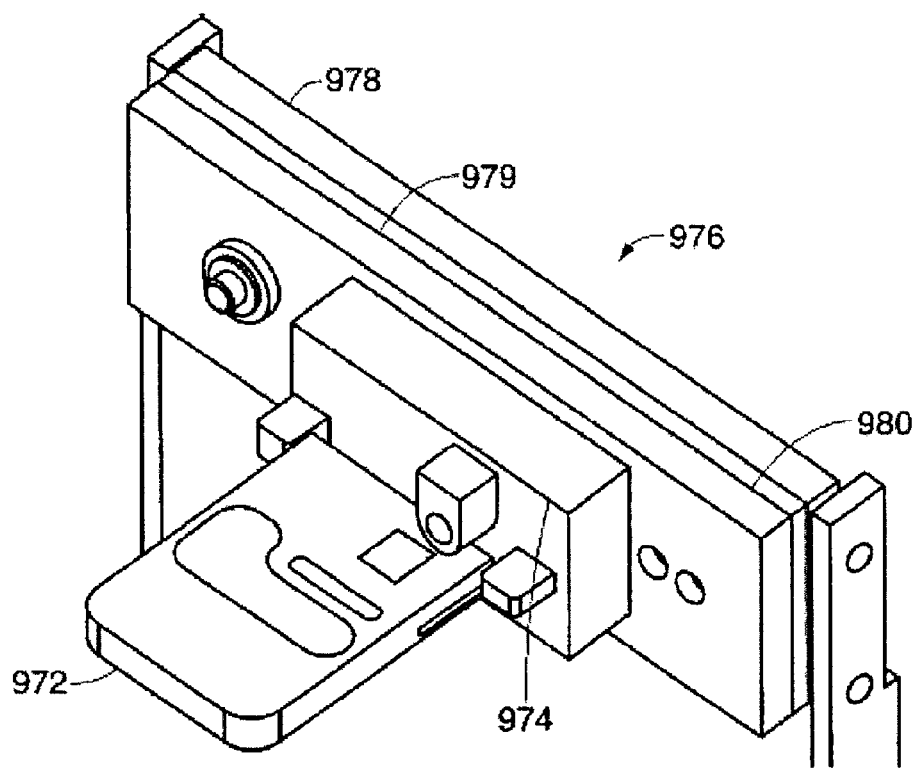
FIG. 23 is an embodiment of a fluid separation conduit cartridge attached to a manifold of an analytical system, in accordance with preferred embodiments.

Typically the system installation can be customized such that the system can be positioned in numerous places in a facility. That is, the dimensions and shapes of the system can be designed for placement of the system in numerous areas of an operating facility, and the functions, e.g. the chromatographic methods, of the system can be tailored to perform innumerable tests desired by an end-user. In preferred embodiments, the system is placed near the sample or process to be monitored. That is, the system may be placed, either fixably or removably mounted, for example, near the fluid to be analyzed. For example, the system can be custom mounted to a conduit 970 that carries a fluid sample, e.g. river water, out of a manufacturing facility, for example. Depending upon the configuration of the system, the system can automatically sample the fluid flowing through the conduit, e.g. using an auto-sampler, auto-injector and the like, or one or more valves positioned in the conduit can be connected to the analytical system for introducing samples into the system. Alternatively, an operator can manually take samples from the conduit and can introduce the samples through a fixed-loop injector, for example, using a needle, syringe, and the like. One skilled in the art given the benefit of this disclosure will be able to select suitable positions for the system described here depending on the type of analyses to be performed by the system The fluid separation conduit cartridge typically interfaces with an analytical system through a manifold, e.g. the multi-layer laminated manifold 976 shown in FIG. 23. In FIG. 23, the conduit cartridge 972 will be understood to be analogous to conduit cartridge 960 shown in FIG. 22. The manifold 976 is seen in the particular embodiment of FIG. 23 to be a multi-layer laminated structure and has one or more microfluidic channels for introducing fluid into or receiving fluid from the fluid separation conduit cartridge. For example, the manifold 976 may comprise a first layer 978 attached to a second layer 979 which itself is attached to a third layer 980. As can be seen in FIG. 23, the second layer 979 typically is sandwiched between the first layer 978 and the third layer 980. Fluid channels can be provided within and/or at the interface(s) of the layers of such manifolds. For example, layer 979 in the manifold 976 of FIG. 23 can optionally be constructed as a microfluidic substrate assembly described in commonly assigned U.S. Patent Application No. 60/239,010 titled "Microfluidic Substrate Assembly and a Method of Making Same" and filed on Oct. 06, 2000, the entire disclosure of which is hereby incorporated herein by reference for all purposes. The layers of the multi-layer laminated manifold each can be manufactured from any of numerous materials, including but not limited to PEEK, steel, e.g. stainless steel, and the like. Different layers of the multi-layer laminated manifold may be formed of different materials. In certain embodiments, the microfluidic flow channel is between two or more of the layers, e.g. the microfluidic flow channel can extend from the third layer into the second layer and optionally into the first layer, for example. The microfluidic flow channel can be formed in one or more of the layers using numerous techniques, e.g. UV embossing, micro-machining, micro-milling, and the like. For example, a microchannel can be etched into the second layer and the first layer such that when the second layer is assembled to the first layer a fluid-tight microfluidic flow channel is created. As discussed above, the layers can be assembled to form the multi-layer laminated manifold. For example, the layers can be assembled by welding the layers together, optionally with a gasket positioned between the layers, or can be assembled using adhesives and the like. One skilled in the art given the benefit of this disclosure will be able to select suitable methods for assembling the layers of multi-layer laminated manifolds suitable for use with the conduit cartridges disclosed here. Preferably, the manifold comprises at least a first microfluidic channel in fluid communication with a solvent reservoir and with the input orifice of the fluid separation conduit cartridge. Thus solvent may flow into the conduit cartridge through a microfluidic channel in the manifold, e.g. by pumping the fluid into the cartridge using a pump. The manifold can include a second microfluidic channel that is in fluid communication with an output orifice of the conduit cartridge and typically is also in fluid communication with a detector. Therefore, a sample may be introduced into the conduit cartridge through the first microfluidic channel in the manifold, separated by the conduit cartridge, and the separated species can flow out of the conduit cartridge through the second microfluidic channel in the manifold to a detector that can measure the amount and nature of the species present in the sample. One skilled in the art given the benefit of this disclosure will be able to design other suitable manifolds and devices for interfacing the conduit cartridge with an analytical system.

The manifold may also contain an interface 974 mounted to the manifold. The interface typically is operative to create a fluid-tight seal when the cartridge is plugged into the manifold. That is, interface 974 is operative to provide a sealing force suitable to prevent fluid from leaking between the manifold and the fluid separation conduit cartridge. Optionally, one or more gaskets can be positioned between the conduit cartridge and the interface to aid in forming a fluid-tight seal. One skilled in the art, given the benefit of this disclosure, will be able to select suitable interfaces and mechanisms for retaining the conduit cartridge against the manifold to create a fluid-tight seal. Exemplary mechanisms include cams, springs, pressure plates, welding, clamps, gear drives, and combinations of any of them, adapted to be actuated by gravity or manually, by solenoid, pneumatically, hydraulically, etc. As discussed above, in alternative embodiments the conduit cartridge is plugged directly into the system without using a manifold. For example, suitable connectors may be added to the conduit cartridge such that the conduit cartridge can be in direct fluid communication with a flow line, e.g. a flow line including one or more solvents and one or more species to be separated. One skilled in the art given the benefit of this disclosure will be able to select suitable mechanisms and devices for interfacing the conduit cartridge disclosed here to a chromatography system.

Figure 24:
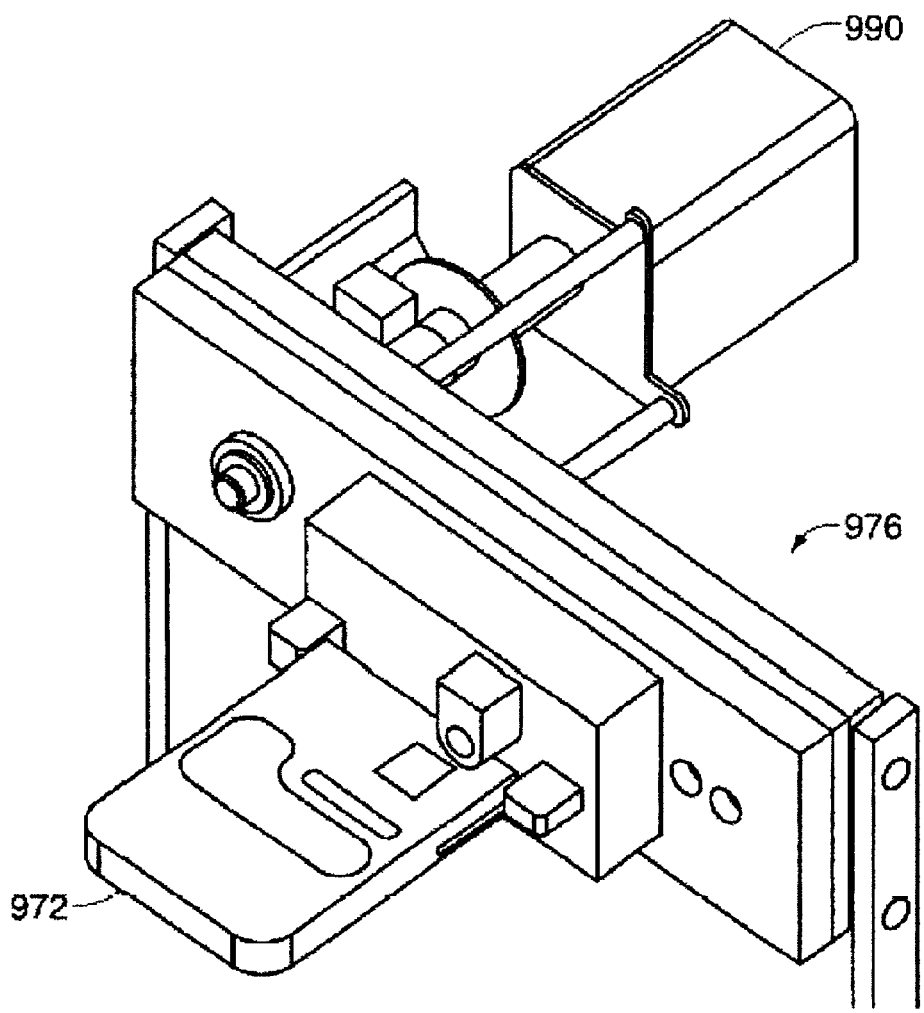
FIG. 24 is an embodiment of a fluid separation conduit cartridge attached to a manifold of an analytical system where the manifold is in fluid communication with a device for generating a fluid flow, in accordance with preferred embodiments.

In other embodiments, the manifold itself is in communication with a device for generating a fluid flow. For example, referring to FIG. 24, a pump 990 can be attached to the manifold and can be configured such that fluid is drawn from a fluid reservoir, e.g. a solvent reservoir, and is forced into the manifold and subsequently into conduit cartridge 972. Such devices may be any of the devices discussed above including but not limited to pumps, vacuum manifolds and the like. The device for generating a fluid flow can also be in communication with one or more injectors as discussed above.

The information that is transmitted from the conduit cartridge to the analytical system can be encrypted as described above. For example, a conduit cartridge and an analytical system in communication with the conduit cartridge may be performing an analysis of components in river water. A remote operator may wish to alter the method used by the analytical system. The operator could transmit a new encrypted method to the cartridge. After receiving new encrypted method, the cartridge can subsequently send the encrypted message to the analytical system to alter the method used for analysis. Remotely receiving information provides for the alteration of the information without having to physically input the new information, using an input pad or comparable device, on the conduit cartridge or on the analytical system.

EXAMPLE 2

Figure 25:
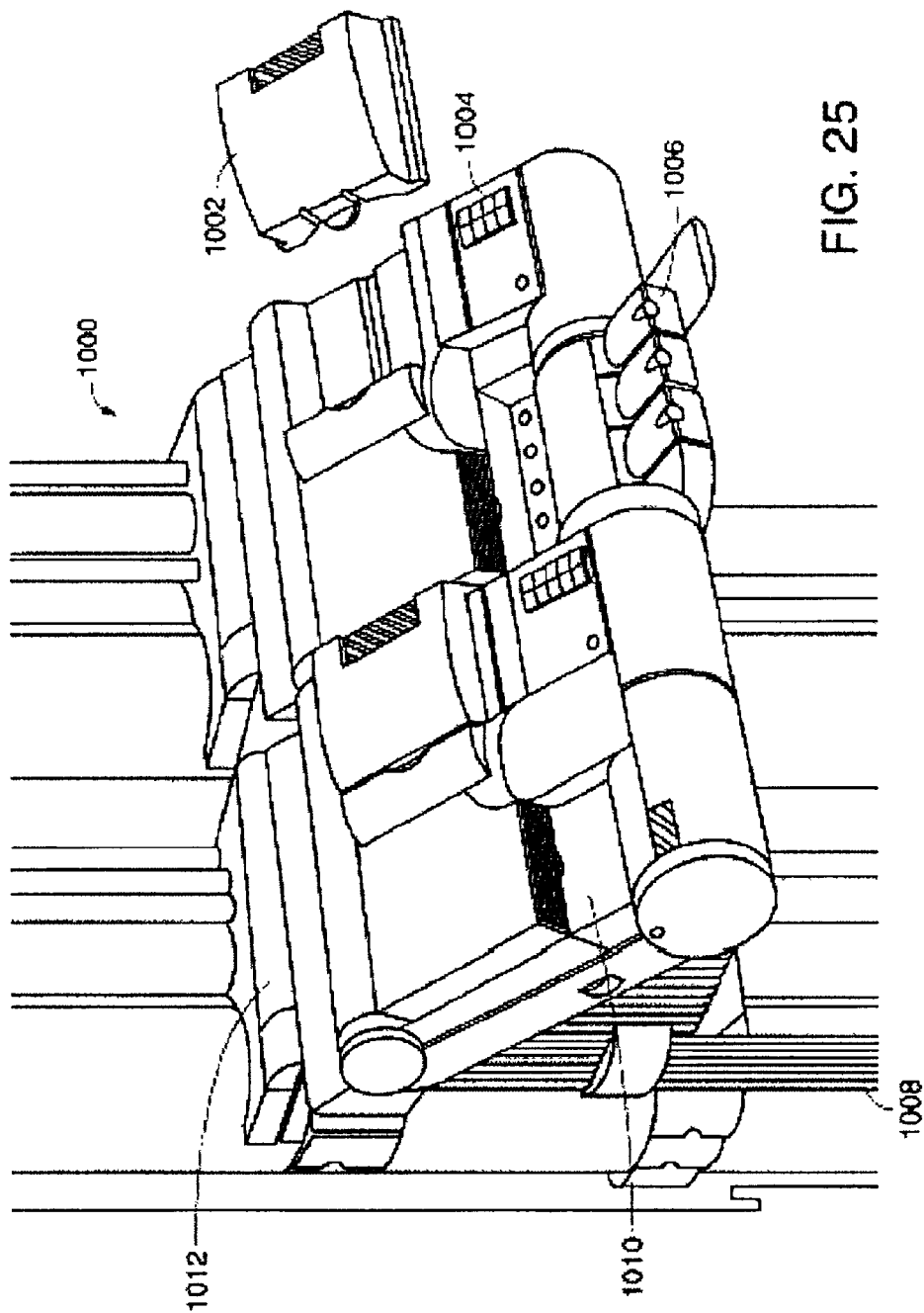
FIG. 25 is a second embodiment of an analytical system in communication with a fluid separation conduit cartridge, in accordance with preferred embodiments.

An additional example of a fluid separation conduit cartridge interfaced with an analytical system is shown in FIG. 25. The analytical system 1000 comprises a fluid separation conduit cartridge 1002, e.g. a cartridge operative to perform capillary liquid chromatography, a graphical user interface 1004, and buffer cassettes 1006. The graphical user interface can be used to program the system and/or the fluid separation conduit cartridge for a specific method, e.g. a specific solvent gradient, run time, flow rate, and the like. As discussed above, the graphical user interface can be omitted in embodiments where the conduit cartridge is operative to program the system, e.g. where the conduit cartridge comprises an analytical method in a memory unit, for example. The buffer cassettes are equivalent to solvent reservoirs. That is, the buffer cassettes may be loaded with any suitable mobile phase needed to perform a chromatographic method, for example. Preferably, the mobile phases are different in different buffer cassettes such that solvent gradients can be implemented in the analytical method. The buffer cassettes may be in communication with one or more devices that are operative to generate a fluid flow (not shown), e.g. pumps and the like. The system 1000 typically has one or more power and communication interfaces 1008 and can be custom installed 1012 at a user's facility such that automated analyses may take place or such that the system is positioned near the fluid to be analyzed. As discussed above, the communication interface may send and/or receive data to or from a central computer, or other device. The system can be controlled by remote operation and diagnosis using a communication device 1010 by various methods, such as for example, e-mail over the Internet. The communication device typically is used to alter the method of the system without having to manually enter the new method using the graphical user interface. This feature provides for remote configuration, or reconfiguration as the case may be, of the system. In certain embodiments, the communication device is omitted and the system is controlled by information sent from the conduit cartridge to the system. As can be seen in FIG. 25, the size of the fluid separation conduit cartridge can be tailored such that it has the appropriate dimensions, e.g. height, width and thickness, and has the appropriate connectors to interface with any analytical system. For example, in embodiments comprising a capillary column, the dimensions of the conduit cartridge may be reduced such that the footprint of the cartridge is smaller and occupies less space on the analytical system. Suitable fluid connectors including those discussed here, e.g. ferrule subassemblies and the like, can be attached to the conduit cartridges and are typically operative to create a fluid-tight seal between the conduit cartridge and the analytical system. Suitable electrical connectors can be attached to the conduit cartridge including those discussed above, for example, PCMCIA connectors, USB connectors, serial connectors and the like. The electrical connectors typically provide for transfer of information to and from the conduit cartridge.

As discussed above, the fluid separation conduit cartridge can interface with the system through a manifold, such as the manifold shown in FIG. 23, or can interface with the system directly, e.g. without any intervening physical components. Suitable connectors for interfacing with the manifold can be positioned on any surface of the housing unit of the conduit cartridge. The fluid separation conduit cartridge 1002 may include one or more connectors on a major surface, e.g. the back surface of the conduit cartridge 1002 shown in FIG. 25, such that the conduit cartridge can interface with a manifold and sit flush with the surface of the system. For example, the conduit cartridge may have outwardly projecting connectors that plug into a manifold, having receiving sockets, positioned on the analytical system. When the conduit cartridge is plugged into the manifold, the conduit cartridge snaps into position on the analytical system, e.g. becomes seated in a slot on the surface of the analytical system. Thus, the conduit cartridge is in fluid communication with the analytical system and is retained by the system such that vibrations will not dislodge the conduit cartridge from the system, i.e. the conduit cartridge remains in fluid communication with the system even in the presence of vibrations or other physical disturbances. Numerous other devices, e.g. cams, pulleys, springs, pressure plates and the like may be used to retain the conduit cartridge against the manifold of the system such that a fluid tight seal is preserved.

Also as discussed above, information that is sent from conduit cartridge to the analytical system can be encrypted and/or compressed. Preferably, public/private key pairs are used to encrypt/decrypt information that is sent by the conduit cartridge or is received by the conduit cartridge. The analytical system may include multiple public/private key pairs. For example, the communications device may have it owns encryption/decryption keys such that information received from a remote operating facility by the communication device is decrypted prior to sending the information to the conduit cartridge. In other embodiments, the communication device decrypts the information and re-encrypts the information using a different key. Once received by the conduit cartridge the information may then be decrypted and a new method, for example, may be implemented by the analytical system. One skilled in the art, given the benefit of this disclosure, will recognize that a conduit cartridge can send information to the communication device and the communication device can subsequently transmit the information. As discussed above, the information can be encrypted and decrypted at numerous devices along the transmission path. In preferred embodiments, the conduit cartridge receives encrypted information from a remote operating facility, decrypts the information, and alters the method of the analytical system in accordance with the information received. That is, the conduit cartridge is operative to receive encrypted information remotely and can alter the method of the analytical system by sending the decrypted information to the system.

Although the present invention has been described above in terms of specific embodiments, it is anticipated that other uses, alterations and modifications thereof will become apparent to those skilled in the art given the benefit of this disclosure. It is intended that the following claims be read as covering such alterations and modifications as fall within the true spirit and scope of the invention. It is intended that the articles "a" and "an", as used below in the claims, cover both the singular and plural forms of the nouns which the articles modify.

What is claimed is:

1. A fluid separation conduit cartridge comprising:
   a housing unit;
   a fluid separation conduit within the housing unit;
   an inlet orifice in fluid communication with a first end of the fluid separation conduit;
   an outlet orifice in fluid communication with a second end of the fluid separation conduit, the fluid separation conduit providing a fluid flow path within the housing unit from the inlet orifice to the outlet orifice; and
   an encryption device mounted to the fluid separation conduit cartridge and operative to perform an encryption operation on a signal communicated between the encryption device and a component in fluid communication with the fluid separation conduit cartridge.

2. The fluid separation conduit cartridge in accordance with claim 1 in which the encryption device is a microprocessor.

3. The fluid separation conduit cartridge in accordance with claim 1 further comprising a memory unit mounted to the housing unit.

4. The fluid separation conduit cartridge in accordance with claim 3 further comprising one or more parameter tables in the memory unit.

5. The fluid separation conduit cartridge in accordance with claim 4 in which the one or more parameter tables are selected from the group consisting of encryption algorithms and compression algorithms.

6. The fluid separation conduit cartridge in accordance with claim 5 in which the encryption algorithm is selected from the group consisting of translation tables, word/byte rotation, Simple Key Management for Internet Protocols (SKIP), XOR bit masking, DES, Blowfish, and MD5.

7. The fluid separation conduit cartridge in accordance with claim 1 further comprising a transmitting and receiving device operative to transmit and receive information.

8. The fluid separation conduit cartridge in accordance with claim 7 in which the transmitting and receiving device operative to transmit and receive information is preferably selected from the group consisting of a modem, a fax machine, a wireless phone, a wireless transmitter, a RF transmitter, and a satellite transmitter.

9. The fluid separation conduit cartridge of claim 7 in which the transmitting and receiving device operative to transmit and receive information transmits and receives information by fax, e-mail, the Internet, or wirelessly.

10. The fluid separation conduit cartridge in accordance with claim 9 in which the transmitted information is encrypted.

11. The fluid separation conduit cartridge in accordance with claim 1 in which the fluid separation conduit is potted with a potting compound.

12. The fluid separation conduit cartridge in accordance with claim 1 in which the encryption device operative to encrypt and decrypt information uses public/private key pairs to encrypt and decrypt information.

13. A method of making a fluid separation conduit cartridge, the method comprising:
    providing an assembled fluid separation conduit cartridge, the assembled fluid separation conduit cartridge comprising
      a housing unit,
      a fluid separation conduit within the housing unit,
      an inlet orifice in fluid communication with a first end of the fluid separation conduit,
      an outlet orifice in fluid communication with a second end of the fluid separation conduit, the fluid separation conduit providing a fluid flow path within the housing unit from the inlet orifice to the outlet orifice, and
      an encryption device mounted to the fluid separation conduit cartridge and operative to perform an encryption operation on a signal communicated between the encryption device and a component in fluid communication with the fluid separation conduit cartridge,
    packing the fluid separation conduit cartridge with appropriate packing material; and
    testing the fluid separation conduit cartridge.

14. The method of claim 13 in which the fluid separation conduit cartridge further comprises a transmitting and receiving device operative to transmit and receive information.

15. The method of claim 14 in which the transmitting and receiving device operative to transmit and receive information is selected from the group consisting of a modem, a fax machine, a wireless phone, a wireless transmitter, a RF transmitter, and a satellite transmitter.

16. The method of claim 13 in which information is encrypted by providing information to an encryption driver and encrypting the provided information using an encryption algorithm.

17. A method of sending information from a fluid separation conduit cartridge, the method comprising:
    providing an assembled fluid separation conduit cartridge, the assembled fluid separation conduit cartridge comprising
      a housing unit,
      a fluid separation conduit within the housing unit,
      an inlet orifice in fluid communication with a first end of the fluid separation conduit,
      an outlet orifice in fluid communication with a second end of the fluid separation conduit, the fluid separation conduit providing a fluid flow path within the housing unit from the inlet orifice to the outlet orifice, and
      an encryption device mounted to the fluid separation conduit cartridge and operative to perform an encryption operation on a signal communicated between the encryption device and a component in fluid communication with the fluid separation conduit cartridge;
    a transmitting and receiving device operative to transmit and receive information;
    encrypting information using an encryption algorithm; and
    transmitting the encrypted information using the transmitting and receiving device.

18. The method of claim 17 in which the transmitting and receiving device operative to transmit and receive information is selected from the group consisting of a modem, a fax machine, a wireless phone or comparable device, a RF transmitter, and a satellite transmitter.

19. The method of claim 17 wherein the transmitted encrypted information is sent to an instrument in fluid communication with the fluid separation conduit cartridge.

20. The method of claim 17 in which the transmitted encrypted information is sent to an operating facility in communication with the fluid separation conduit cartridge.

21. A method of receiving information using a fluid separation conduit cartridge, the method comprising:
   providing an assembled fluid separation conduit cartridge, the assembled fluid separation conduit cartridge comprising
      a housing unit,
      a fluid separation conduit within the housing unit,
      an inlet orifice in fluid communication with a first end of the fluid separation conduit,
      an outlet orifice in fluid communication with a second end of the fluid separation conduit, the fluid separation conduit providing a fluid flow path within the housing unit from the inlet orifice to the outlet orifice,
      an encryption device mounted to the fluid separation conduit cartridge and operative to perform an encryption operation on a signal communicated between the encryption device and a component in fluid communication with the fluid separation conduit cartridge, and
      a transmitting and receiving device operative to transmit and receive information;
   transmitting encrypted information to the assembled fluid separation conduit cartridge; and
   receiving the encrypted information using the transmitting and receiving device operative to transmit and receive information.

22. The method of claim 21 further comprising the step of decoding the received encrypted information.

23. The method of claim 21 in which the transmitted encrypted information is sent from an instrument in fluid communication with the fluid separation conduit cartridge.

24. The method of claim 21 in which the transmitted encrypted information is sent from an operating facility in communication with the fluid separation conduit cartridge.

25. An analytical system comprising:
   a fluid flow channel;
   a fluid separation conduit cartridge;
   a detector; and
   an encryption device operative to perform an encryption operation on a signal communicated between the encryption device and another component of the analytical system;
   the fluid separation conduit cartridge being in fluid communication with the fluid flow channel and comprising
      a housing unit,
      a fluid separation conduit within the housing unit,
      an inlet orifice in fluid communication with a first end of the fluid separation conduit, and
      an outlet orifice in fluid communication with a second end of the fluid separation conduit and in fluid communication with the detector, the fluid separation conduit providing a fluid flow path within the housing unit from the inlet orifice to the outlet orifice.

26. The analytical system of claim 25 further comprising a device for generating fluid flow.

27. The analytical system of claim 25 in which the encryption device is mounted to the fluid separation conduit cartridge.

28. The analytical system of claim 25 in which the encryption device is operative to receive and decrypt an encrypted signal from a remote source.

29. The analytical system of claim 25 in which the encryption device is operative to receive and encrypt a signal from the detector corresponding to information regarding a test sample.

30. The analytical system of claim 25 in which the encryption device comprises a memory unit storing an encryption key.

31. The analytical system of claim 30 in which the memory unit is mounted to the housing unit.

* * * * *